United States Patent
Branch et al.

(10) Patent No.: US 7,665,167 B2
(45) Date of Patent: Feb. 23, 2010

(54) METHOD AND APPARATUS FOR ALIGNING A KNEE FOR SURGERY OR THE LIKE

(75) Inventors: Thomas P. Branch, 930 Lullwater Rd., Atlanta, GA (US) 30307; Alexander Sattler, Jr., Marietta, GA (US); Fredrik Westin, Decatur, GA (US)

(73) Assignee: Thomas P. Branch, Atlanta, GA (US)

( * ) Notice: Subject to any disclaimer, the term of this patent is extended or adjusted under 35 U.S.C. 154(b) by 1094 days.

(21) Appl. No.: 11/077,964

(22) Filed: Mar. 11, 2005

(65) Prior Publication Data

US 2005/0222573 A1 Oct. 6, 2005

Related U.S. Application Data

(60) Provisional application No. 60/552,641, filed on Mar. 11, 2004.

(51) Int. Cl.
*A61G 13/12* (2006.01)
*A61B 17/56* (2006.01)

(52) U.S. Cl. .............. 5/624; 5/621; 5/648; 5/651; 128/882; 602/36

(58) Field of Classification Search .............. 5/624, 5/621, 648–651, 602, 619; 128/882; 602/32, 602/33, 36, 39, 40
See application file for complete search history.

(56) References Cited

U.S. PATENT DOCUMENTS

| | | | | |
|---|---|---|---|---|
| 4,407,277 A | * | 10/1983 | Ellison | 602/39 |
| 4,443,005 A | * | 4/1984 | Sugarman et al. | 5/651 |
| 4,524,766 A | | 6/1985 | Petersen | |
| 4,615,516 A | | 10/1986 | Stulberg et al. | |
| 4,913,413 A | | 4/1990 | Raab | |
| 5,056,535 A | * | 10/1991 | Bonnell | 128/882 |
| 5,571,110 A | | 11/1996 | Matsen, III et al. | |
| 5,606,590 A | | 2/1997 | Petersen et al. | |
| 5,645,079 A | * | 7/1997 | Zahiri et al. | 5/610 |
| 6,669,660 B2 | * | 12/2003 | Branch | 602/13 |
| 6,684,095 B1 | | 1/2004 | Bonutti | |
| 2005/0222573 A1 | * | 10/2005 | Branch et al. | 606/86 |

FOREIGN PATENT DOCUMENTS

GB 2 262 435 A 6/1993

OTHER PUBLICATIONS

International Search Report; International Application No. PCT/US2005/008353; dated Dec. 21, 2005.
International Search Report from International Application No. PCT/US2005/008353; dated Aug. 19, 2005.

* cited by examiner

*Primary Examiner*—Robert G Santos
(74) *Attorney, Agent, or Firm*—Alston & Bird LLP

(57) ABSTRACT

Generally described the invention relates to methods and apparatuses for aligning the lower extremities of a patient with a mechanical axis. More specifically, the present invention provides an exoskeleton or external framework that positions a patient's leg into a desired mechanical axis in preparation for surgery or other medical treatment.

16 Claims, 16 Drawing Sheets

METHOD AND APPARATUS FOR ALIGNING A KNEE FOR SURGERY OR THE LIKE

CROSS REFERENCE SECTION

This application claims the benefit and priority of U.S. Provisional Application No. 60/552,641, filed Mar. 11, 2004, which is incorporated herein in its entirety.

FIELD OF THE INVENTION

The present invention is generally related to the manipulation of a leg to provide surgery thereon or other medical attention thereto. More specifically, the present invention provides an external frame, or "exoskeleton" to position the leg into a desired axis in preparation for surgery or other treatment on the knee.

BACKGROUND OF THE INVENTION

Damage to the weight-bearing surfaces of the knee as a result of arthritis and/or trauma can be isolated to one compartment, or can be global (involving two or more of the three compartments of the knee). The three compartments of the knee are the patellofemoral compartment, the medial compartment and the lateral compartment. When damage to the knee results in a change in the shape of the underlying bone of the knee, the damage is permanent. Surface replacement procedures such as a total knee arthroplasty (TKA) and a unicompartmental knee arthroplasty (UKA) are typical corrective measures for this damage.

The natural biomechanics of the knee places the weight-bearing axis in a position to allow approximately 60% of the weight bearing by the medial compartment and 40% by the lateral compartment of the knee. This weight-bearing axis is measured in the frontal plane and is a line drawn from the center of the femoral head to the center of the ankle. Therefore, this line must fall slightly to the medial side of the center of the knee to accomplish this weight-bearing distribution. Load distribution across the knee corresponds to the relative surface area of each compartment. That is to say, the medial compartment is generally 60% of the total bearing surface area of the knee. The body distributes this weight optimally to maintain a certain amount of load per square inch of surface area. When this load exceeds a certain level in one or the other compartment, overload in that compartment occurs and damage ensues. The damage begins with articular cartilage wear and can progress to flattening of the condyle with its resultant shape change in the condyle.

When only one compartment in the knee has been damaged permanently, a unicompartmental knee arthroplasty or UKA is used to replace the damaged bone surface. This type of prosthesis has several common failure modes: 1) the side with the UKA fails due to poly wear or interface failure; 2) the opposite compartment fails due to a substantial increase in arthritis; and 3) the femoral component impinges on the patella creating an impingement syndrome. Each of these failures can be attributed to misalignment of the implant. Therefore, there is great need when performing a UKA to implant the device such that the proper mechanical axis within the knee is recreated. Since every lower extremity is unique, the mechanical axis must be uniquely reproduced for the best chance at long-term success. When installed in alignment with the proper axis, the UKA survival rate is greatly improved.

Total Knee Arthoplasty or TKA is a surgical procedure wherein both the lateral and medial compartments are replaced. The proper mechanical axis for these procedures is also important to the long-term success of the implant.

Several prior art devices have been used for the purpose of establishing an axis for partial and total knee replacement surgery. One procedure involves forcing a metal rod into the end of the thighbone. The surgeon then uses this rod to estimate the proper angle for cutting the bone and installing the prosthesis. This procedure has numerous disadvantages including inaccurate cutting of the bone resulting in incorrect placement of the prosthesis and blood clots that may occur from forcing the rod into the marrow of the thighbone to estimate the mechanical axis.

An additional method for aligning the bones for a knee replacement surgery is a device called an intramedullary guidance system. This device takes measurements of the leg and calculates the proper alignment. However, the measurements tend to be inaccurate because they are taken from the somewhat deformable tissue covering the bone rather than the more rigid bone itself. As a result, the alignment measurements vary based on the amount of tissue covering the bone.

Once the axis is estimated using one of the techniques described above, a cutting guide is secured to the bone, which requires multiple incisions. The securing process may weaken the bone and increase the recovery time.

An additional factor in the placement of a knee prosthesis is the natural amount of 'play' in the joint. This 'play' is defined as the natural amount of motion between the two bones of the joint allowed by the ligaments. In a knee joint with a lot of "play," incongruous joint surfaces will still allow full flexion and extension. On the other hand, a knee joint with very little 'play' must have perfectly shaped joint surfaces to allow full flexion and extension. One job of the surgeon during implantation of either a TKA or a UKA is the need to recreate the patient's normal amount of joint 'play'. This means the appropriate amount of ligament release and implant size must be used to allow for both the appropriate amount of 'play' and correction of the mechanical axis. The current known methods do not provide a method of determining the natural play of a joint.

Therefore there is a need for methods and apparatuses for the alignment of a leg for surgery or other medical attention that address deficiencies in the art, some of which are discussed above.

SUMMARY OF THE INVENTION

The present invention provides improvements over the prior art by providing a method and apparatus for aligning a leg in order to facilitate surgery or medical treatment thereon.

Therefore it is an object of the present invention to provide an improved medial device and technique of using same.

It is a further object of the present invention to provide an improved method and apparatus for aligning a knee joint of a patient.

It is a further object of the present invention to provide an improved method and apparatus for aligning a knee of a patient for the purposes of knee replacement surgery.

It is a further object of the present invention to provide an improved method and apparatus for assessing the natural play associated with a knee joint.

It is a further object of the present invention to provide an improved method and apparatus for aligning the knee while in a bent condition.

It is a further object of the present invention to provide a method and apparatus to increase the speed of knee replacement surgery.

It is a further object of the present invention to provide an improved method and apparatus to reduce the number of persons required to perform a UKA or TKA.

It is a further object of the present invention to provide an improved method and apparatus to reduce the need for drilling into bone to secure cutting guides during knee replacement surgery.

It is a further object of the present invention to provide an inflatable bladder under the thigh to provide distraction of the knee joint when the leg is in the bent or flexion position.

In an aspect of the present invention, an apparatus is provided for identifying the mechanical axis of a leg of a patient to facilitate medical treatment thereon, the leg including a femoral head, and a foot portion which itself includes an ankle portion, the mechanical axis having a portion extending from the center of the femoral head to the center of the ankle, the apparatus including a base member including a spine portion and a head portion, the spine portion being substantially elongate and having a longitudinal axis, the head portion attached proximate one longitudinal end of the spine portion, a pelvic location assembly attached relative to the base member proximate the head portion, the pelvic location assembly including a femoral head location member configured to identify the approximate location the femoral head of the leg, the pelvic location assembly also configured to establish a first reference point positioned at a known location relative to the center of the femoral head, a carriage moveably attached relative to the spine portion and configured to be moved along a carriage path having a portion being substantially parallel to the longitudinal axis of the spine, and the carriage further configured to be selectively secured relative to the spine so as to discourage the relative movement between the carriage and the spine, a boot assembly pivotably attached relative to the carriage and configured to accept the foot portion of the leg and to establish a second reference point at a known location relative to the center of the ankle portion, and a mechanical axis indicator providing a visual indication of a portion of a reference axis passing through from the first reference point and through to the second reference point, the reference axis being within substantially the same plane as the mechanical axis.

In a further aspect of the present invention, an apparatus is provided for aligning a leg of a patient with a mechanical axis to facilitate medical treatment thereon, the leg including a femoral head, a thigh portion and a foot portion which itself includes an ankle portion, the mechanical axis having a portion extending from the center of the femoral head to the center of the ankle, the apparatus including a base member including a spine portion and a head portion, the spine portion being substantially elongate and having a longitudinal axis, the head portion attached proximate one longitudinal end of the spine portion, a pelvic location assembly attached relative to the base member proximate the head portion, the pelvic location assembly including a femoral head location member configured to identify the approximate location the femoral head of the leg, the pelvic location assembly also configured to establish a first reference point positioned at a known location relative to the center of the femoral head, a carriage moveably attached relative to the spine portion, and configured to be moved along a carriage path having a portion being substantially parallel to the longitudinal axis of the spine, the carriage further configured to be selectively secured relative to the spine so as to discourage the relative movement between the carriage and the spine, a boot assembly pivotably attached relative to the carriage and configured to accept the foot portion of the leg and to establish a second reference point at a known location relative to the center of the ankle portion, a mechanical axis indicator providing a visual indication of a portion of a reference axis passing through from the first reference point and through to the second reference point, such that the reference axis is within substantially the same plane as the mechanical axis, a leg manipulation assembly attached relative to the spine portion between the pelvic location assembly and the boot assembly, the leg manipulating assembly having a first lateral force assembly and a second lateral force assembly the force assemblies being proximate the thigh portion and spaced apart to accept the leg therebetween and located proximate the knee joint, the first lateral force assembly being adjustable and selectably securable along an axis substantially perpendicular to the longitudinal axis of the spine and configured to discourage the leg from moving away from a desired alignment with the mechanical axis indicator.

In another aspect of the present invention, an apparatus is provided for aligning a leg of a patient with a mechanical axis to facilitate medical treatment thereon, the leg including a femoral head, a thigh portion, a knee portion and a foot portion which itself includes an ankle portion, the mechanical axis having a portion extending from the center of the femoral head to the center of the ankle, the apparatus including a base member including a spine portion and a head portion, the spine portion being substantially elongate and having a longitudinal axis, the head portion attached proximate one longitudinal end of the spine portion, a pelvic location assembly attached relative to the base member proximate the head portion, the pelvic location assembly including a femoral head location member configured to establish a first reference point positioned at a known location relative to the center of the femoral head, a carriage moveably attached relative to the spine portion and configured to move along a carriage path having a portion being substantially parallel to the longitudinal axis of the spine and further configured to be selectively secured relative to the spine so as to discourage the movement, a boot assembly pivotably attached relative to the carriage and configured to accept the foot portion of the leg and to establish a second reference point at a known location relative to the center of the ankle portion, a upper pivoting assembly having a first end pivotably attached relative to the spine portion proximate the head portion, a second end pivotably and moveably attached relative to the spine portion and a hinged portion positioned proximate the patient's knee between said first end and said second end such that when said patient's knee is in a bent condition, said second end moves relative to said spine portion and said hinge portion follows said knee such that said thigh support member also provides support to said thigh portion of said leg, a mechanical axis indicator providing a visual indication of a reference axis passing through said first reference point and through the second reference point, such that the reference axis is within substantially the same plane as the mechanical axis, and a leg manipulation assembly attached relative to the spine portion between the pelvic location assembly and the boot assembly, the manipulating assembly having a first lateral force assembly and a second lateral force assembly being spaced apart to accept the leg therebetween and located proximate the knee joint, the first lateral force assembly being adjustable and selectably securable in an axis substantially perpendicular to the longitudinal axis of the spine and configured to urge the leg into alignment with the mechanical axis identifier.

In a further embodiment of the present invention, an apparatus is provided that is configured to measure the clearance between the mating surfaces of the femur and a tibia at the knee joint, the apparatus being elongate with a substantially wedge shaped tip portion, the wedged shaped tip portion including indicia associated with a width at a distance spaced apart from the end of the wedge shaped tip.

It is to be understood that the inventions are not to be limited to the specific embodiments disclosed and that modifications and other embodiments are intended to be included within the scope of the present invention. Although specific terms are employed herein, they are used in a generic and descriptive sense only and not for purposes of limitation.

Other objects, features, and advantages of the present invention will become apparent upon reading the following detailed description of the preferred embodiment of the invention when taken in conjunction with the drawing and the appended claims.

DESCRIPTION OF THE DRAWINGS

FIGS. 3A, B is an illustrative views of a portion (from the waist down) of a patient and a portion of an embodiment of the present invention. This view may be considered a top plan view of a patient in the prone position, looking down from above the operating table the patient is lying on.

DETAILED DISCUSSION OF THE PRESENT EMBODIMENT

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

General Construction and Operation

Figure 1:
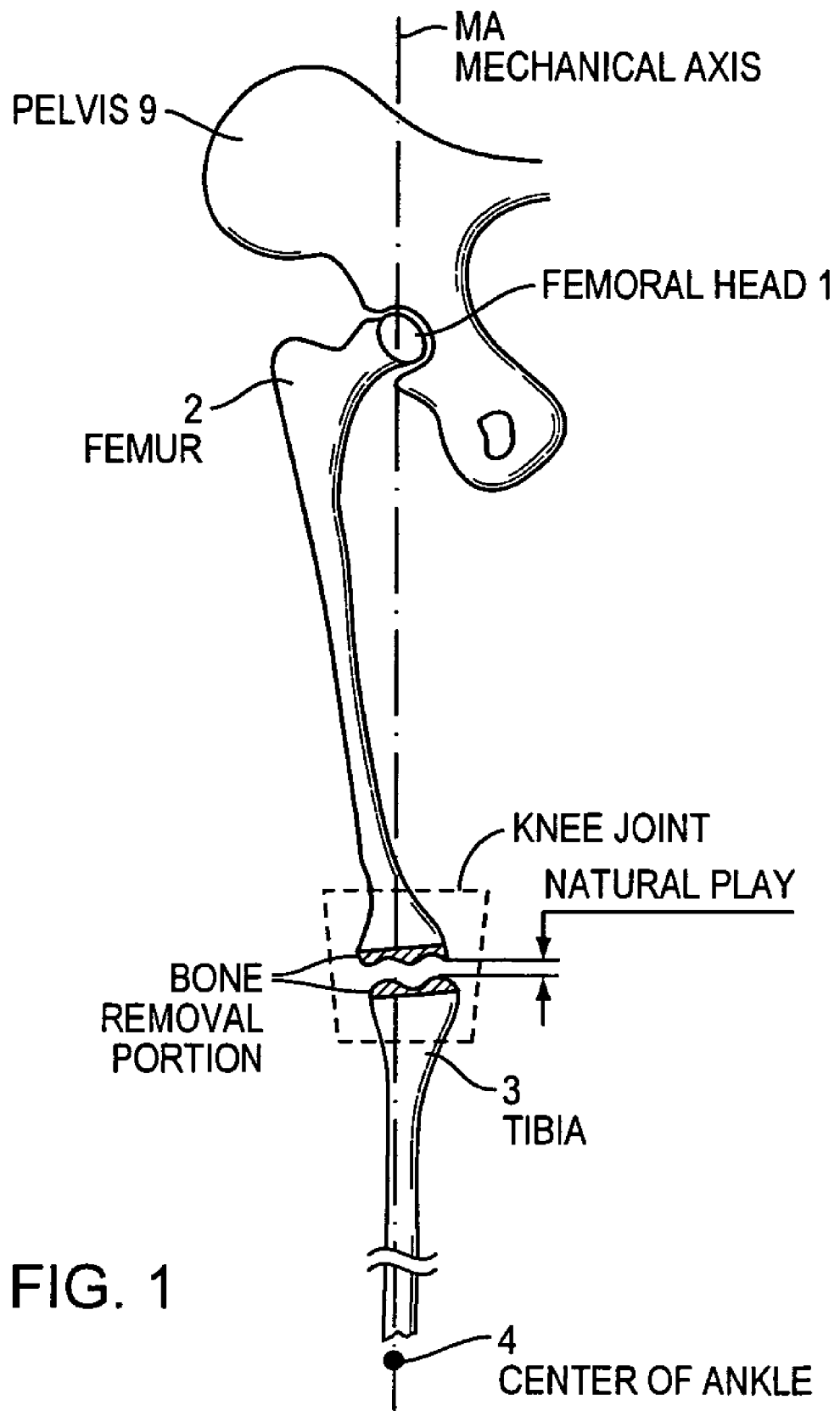
FIG. 1 illustrates certain bones in a typical human leg. As may be seen, the femur 2 extends from a pelvis 9, to a knee joint. A tibia 3 extends from the knee joint to an ankle (not shown). The mechanical axis (MA) is created by a line running through the femoral head and the center of the ankle 4.

Generally described, the invention relates to a method and apparatus for manipulating a human leg into a desired alignment in preparation for surgery or other medical treatment. Referring generally to FIG. 1, the mechanical axis MA of a patient's leg is created by a line stretching from the femoral head 1 of the femur 2 to the center of the ankle 4. In a preferred embodiment, an external framework, or "exoskeleton" provides a visual indication of a reference axis which is within the same vertical plane as the proper mechanical axis MA. This framework also provides a means for manipulating the patient's leg into a desired alignment with the visual indication.

Preferably, a patient's leg is aligned with its mechanical axis when the reference axis created by the present invention is positioned slightly to the medial side of the patient's knee. This alignment achieves an optimum weight distribution at the knee joint when the patient is standing. However, as one of ordinary skill will appreciate, any desired alignment with respect to the reference axis may be achieved using the present invention.

In addition to positioning the patient's leg into proper alignment, an embodiment of the present invention also provides an alignment feature for surgical cutting guides. In this embodiment, a patient's leg and a surgeon's cutting guides are held in an optimal relative position by an external framework. In the prior systems, the leg is manually restrained in its current position, which may or may not be the proper mechanical axis. The surgeon then estimates the adjustment angle necessary to place the knee in its proper mechanical axis when the prosthesis is installed and adjusts the cutting guides accordingly. The success of the surgery is directly related to estimate made by the surgeon, which is dependent on the skill and experience of the surgeon. With embodiments of the present invention, the surgeon no longer has to estimate the cut angle on the femur and tibia to achieve the proper mechanical axis MA to facilitate proper installation of a knee prosthesis because the optimum angle is established by the external framework. Thus, the consistency and accuracy of the cutting operation is improved with the use of embodiments of the present invention.

Figure 3B:
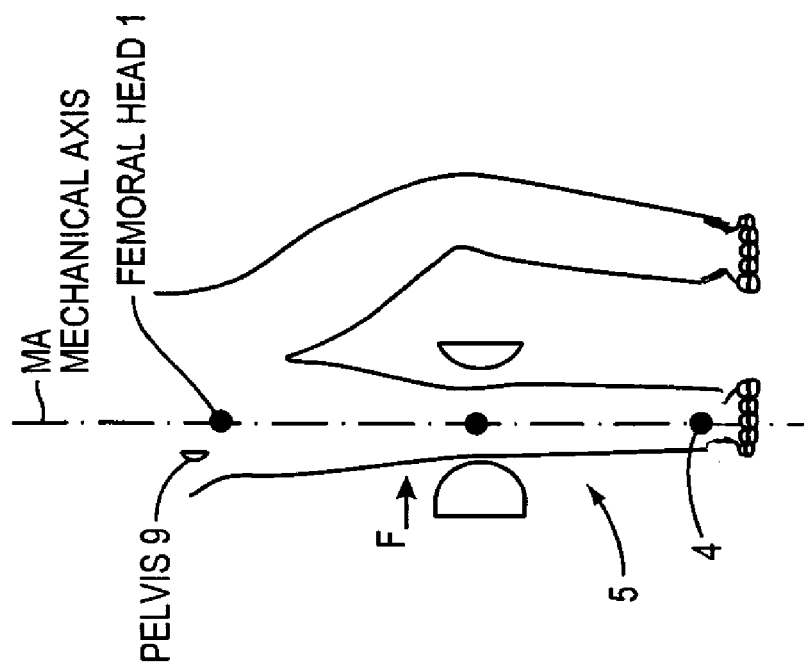
Figure 3A:
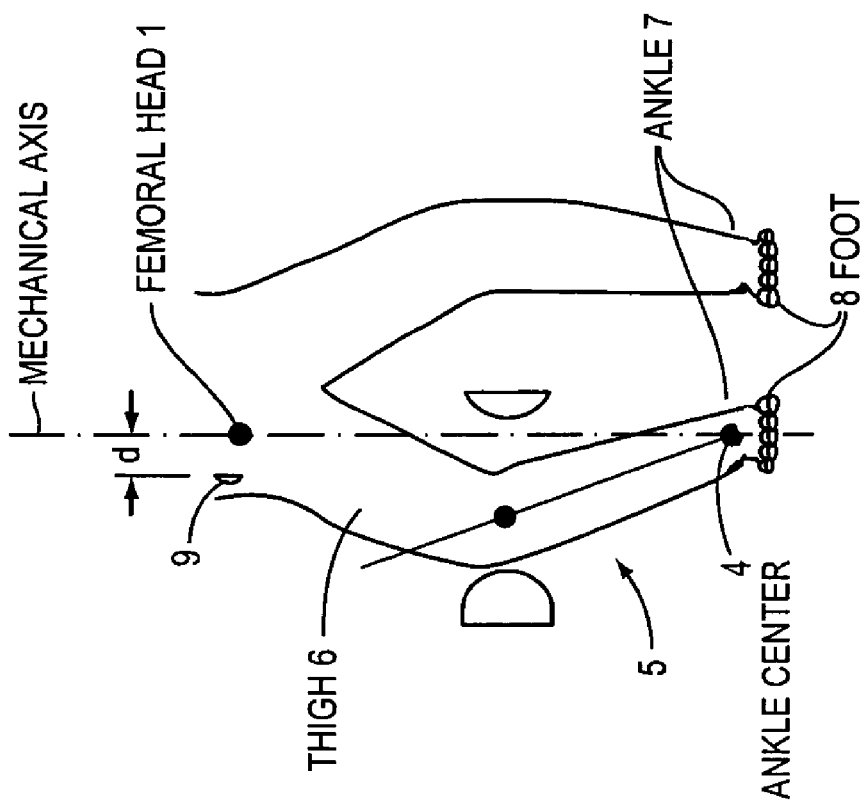

Reference is now made to FIGS. 3A and 3B to further discuss the general operation of the invention. This figure shows a patient's legs in a prone position; the leg designated as 5 has a thigh portion 6, an ankle portion 7 and a foot portion 8. The preferred mechanical axis MA for the patient's leg 5 is created by a line running through the femoral head 1 and the center of the ankle 4. Because the femoral head 1 is not detectable from outside the body, a skeletal reference point that is detectable from outside the body is chosen to aid in locating the femoral head 1. Preferably, the anterior superior iliac spine, which is the bony prominence of the pelvis (i.e. edge of the pelvis 9), is chosen as the skeletal reference point. An X-ray of the patient is used to determine the distance "d" from the skeletal reference point to the femoral head 1. This distance "d" is used to approximate the location of the femoral head based on the skeletal reference point on the patient's body. A reference axis is then created using a cable, string, or laser that is within the same plane as the mechanical axis MA which passes through the femoral head and the center of the ankle.

As best shown in FIG. 3A, the patient's leg 5 may not be in alignment with the mechanical axis MA prior to treatment. To place the leg in proper alignment, a force is applied in the direction of vector "F." FIG. 3B illustrates an aspect of the present invention where an inflated bladder creates a lateral force in the direction of vector F to urge the leg into alignment with the reference axis and therefore the preferred mechanical axis.

Figure 2A:
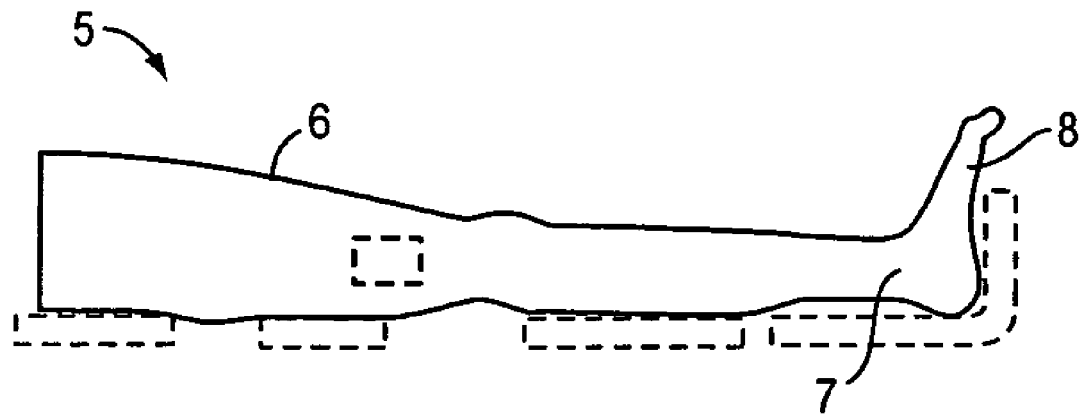
FIGS. 2A and 2B are other illustrative views of a leg of a patient and a portion of an embodiment of the present invention. This view may be considered a side plan view of a patient in a prone position and looking at the patient from the patient's right side.
Figure 2B:
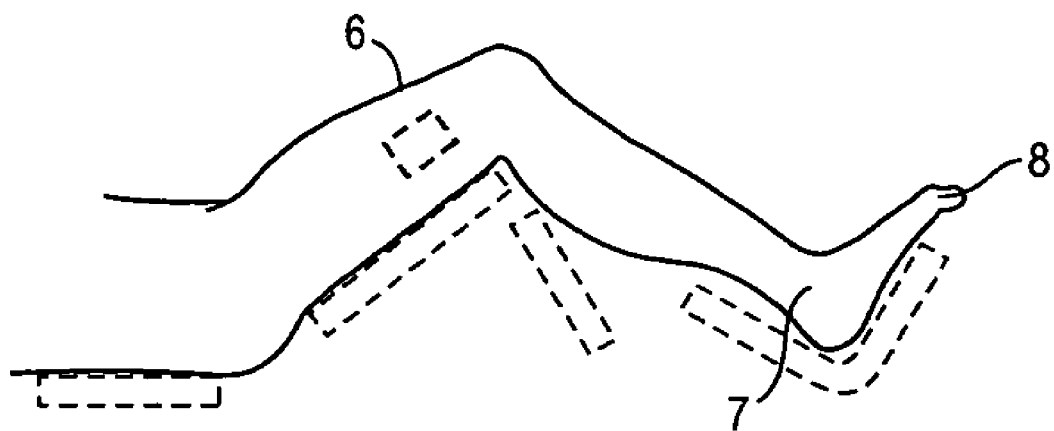

Turning to FIGS. 2A and 2B, a further aspect of the present invention is illustrated where the leg 5 of the patient may be bent without losing alignment with the mechanical axis MA. As illustrated, leg support is provided by the external framework proximate the thigh portion of the leg thereby securing the knee in both the straight and bent positions. Additionally, an inflatable bladder may be positioned under the thigh to allow the surgeon to selectively distract the knee joint by inflating/deflating the bladder. These features allow the surgeon to bend the knee to a desired degree to provide access to the cut portions of the tibia and femur as discussed in greater detail elsewhere in this application.

When a surgeon is performing a partial knee replacement, it is important that the distance between the bearing surfaces of the femur 2 and the tibia 3 is consistent. Therefore, a surgeon measures the distance between the undamaged bearing surfaces of the knee and replicates that distance with the prosthesis. In an additional aspect of the present invention, a tool is provided for measuring this distance.

Figure 13A:
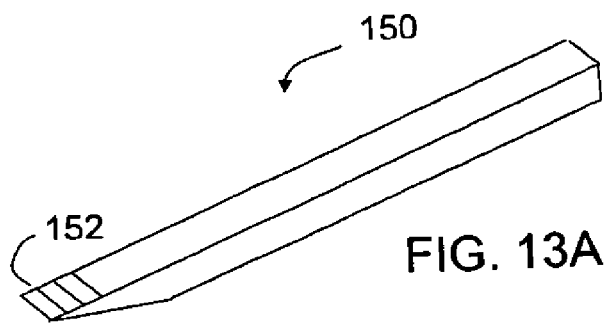
FIGS. 13A and 13B are drawings illustrating two embodiments of the measurement tool 150 in accordance with the present invention.

Referring to FIG. 13A, a measurement tool 150 is provided for measuring the natural play in a knee joint. The measurement tool 150 is generally elongate and has a wedge-shaped measuring portion 152 wherein indicia representing the width of the wedge at different distances from the tip are provided.

Figure 13B:
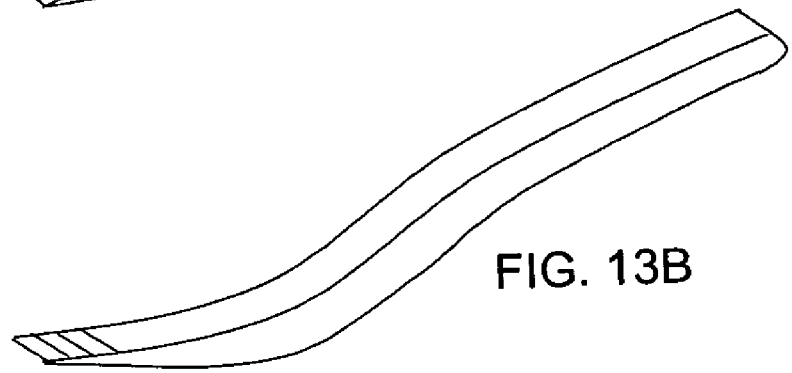

In use, the leg of the patient is positioned in straight condition and distracted by applying a force proximate the foot directed away from the patient's torso. The detraction preferably extends the ligaments of the knee to their maximum length. The wedge-shaped measuring portion 152 of the measuring tool 150 is placed between the bearing surfaces of the femur and tibia until the surfaces of the wedge contact both bearing surfaces. The surgeon reads the indicia corresponding with the depth of the wedge to determine the distance between the bearing surfaces. From this measurement, the surgeon can calculate the amount of bone to remove to achieve the same "play" with the prosthetic joint. FIG. 13B illustrates an alternative embodiment of the measurement tool 150 where the tool takes a more ergonomic shape.

More Detailed Discussion

Apparatus 10

Figure 4:
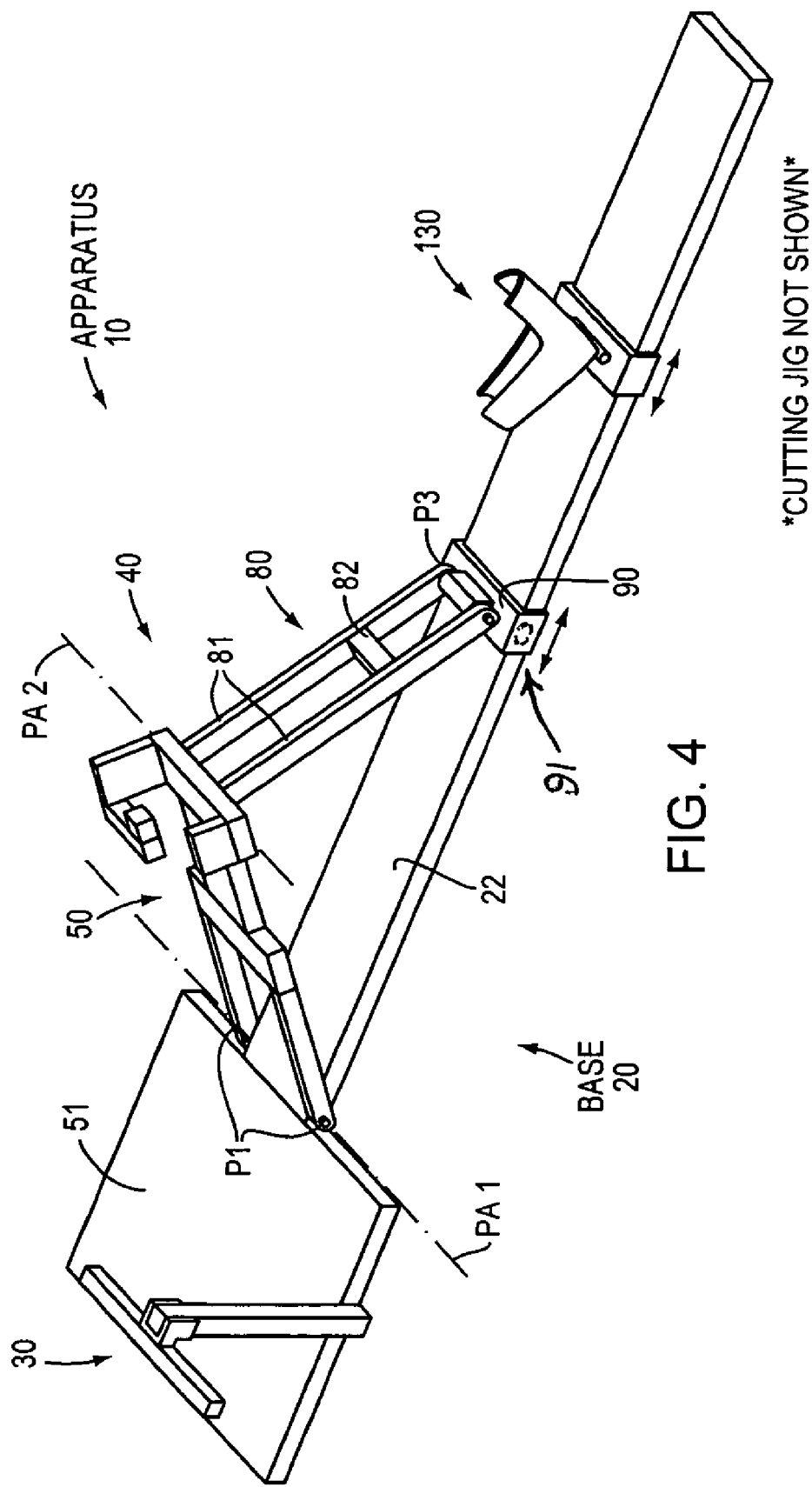
FIG. 4 is a simplified drawing of a portion of apparatus 10 in accordance with one embodiment of the present invention.
Figure 5:
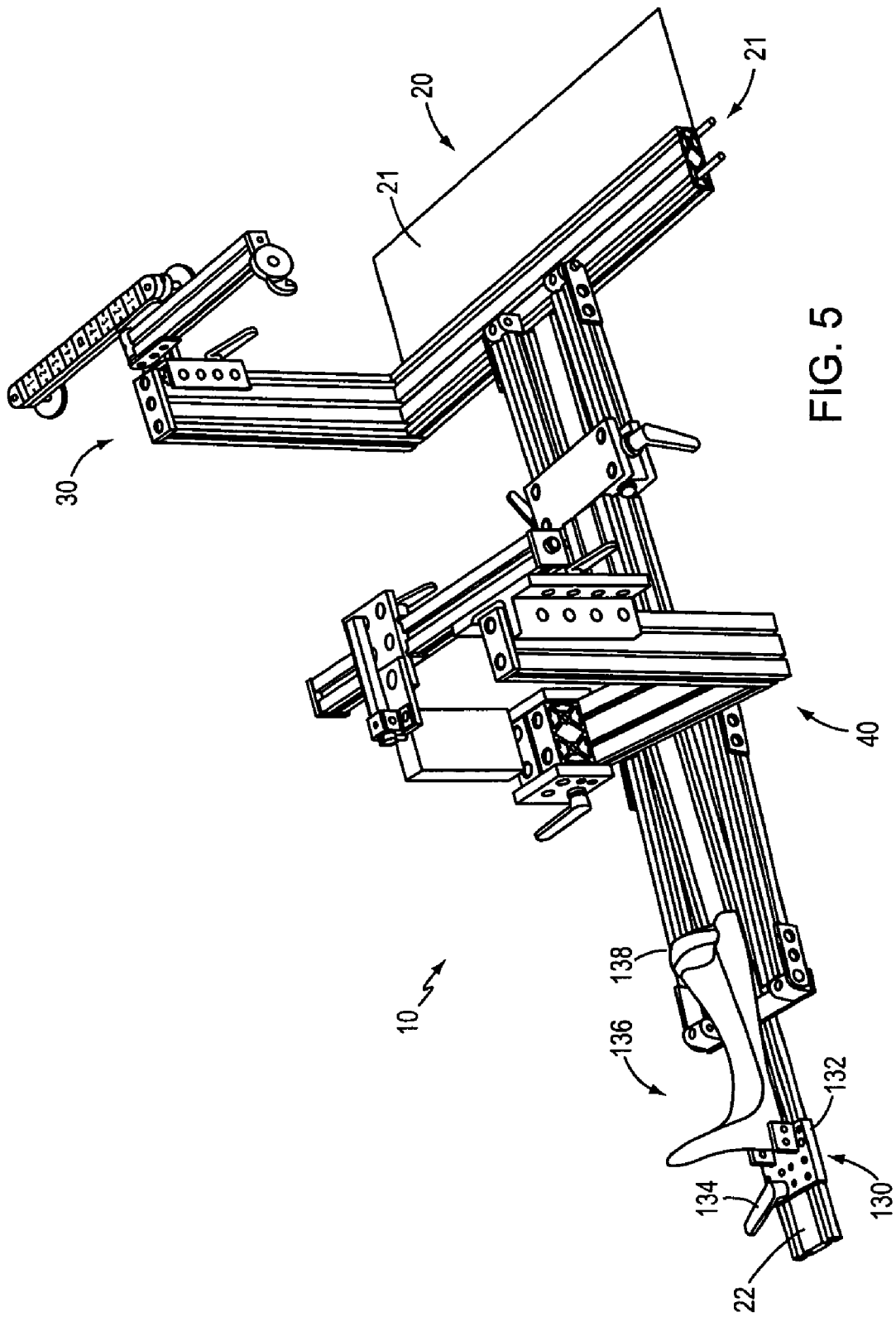
FIG. 5 is a drawing of apparatus 10 shown in an extended configuration in accordance with an embodiment of the present invention.

The apparatus 10 is shown generally in FIGS. 4 and 5. This apparatus 10 is used to manipulate a leg of a user (not shown) in order to provide medical attention thereto. Generally described, the apparatus 10 includes a stationary base 20, a pelvic location assembly 30, a leg manipulation assembly 40, an upper pivoting assembly 50, a lower pivoting member 80, a carriage 90, and a foot assembly 130.

Stationary Base 20

The stationary base 20 is configured to be positioned atop a stationary, substantially horizontal surface, which may be a floor, a suitable medical table, or the like. This stationary base 20 is substantially rigid, and includes a planar head portion 21 fixed to a spine member 22. The planar head portion 21 is configured to support the posterior of a patient (not shown). Padding or the like may be positioned atop the planar head portion as desired. The spine member 22 is essentially elongate, and is configured to accept various carriages to slide along at least a portion of its length as discussed later in this application.

Pelvic Location Assembly 30

Figure 6:
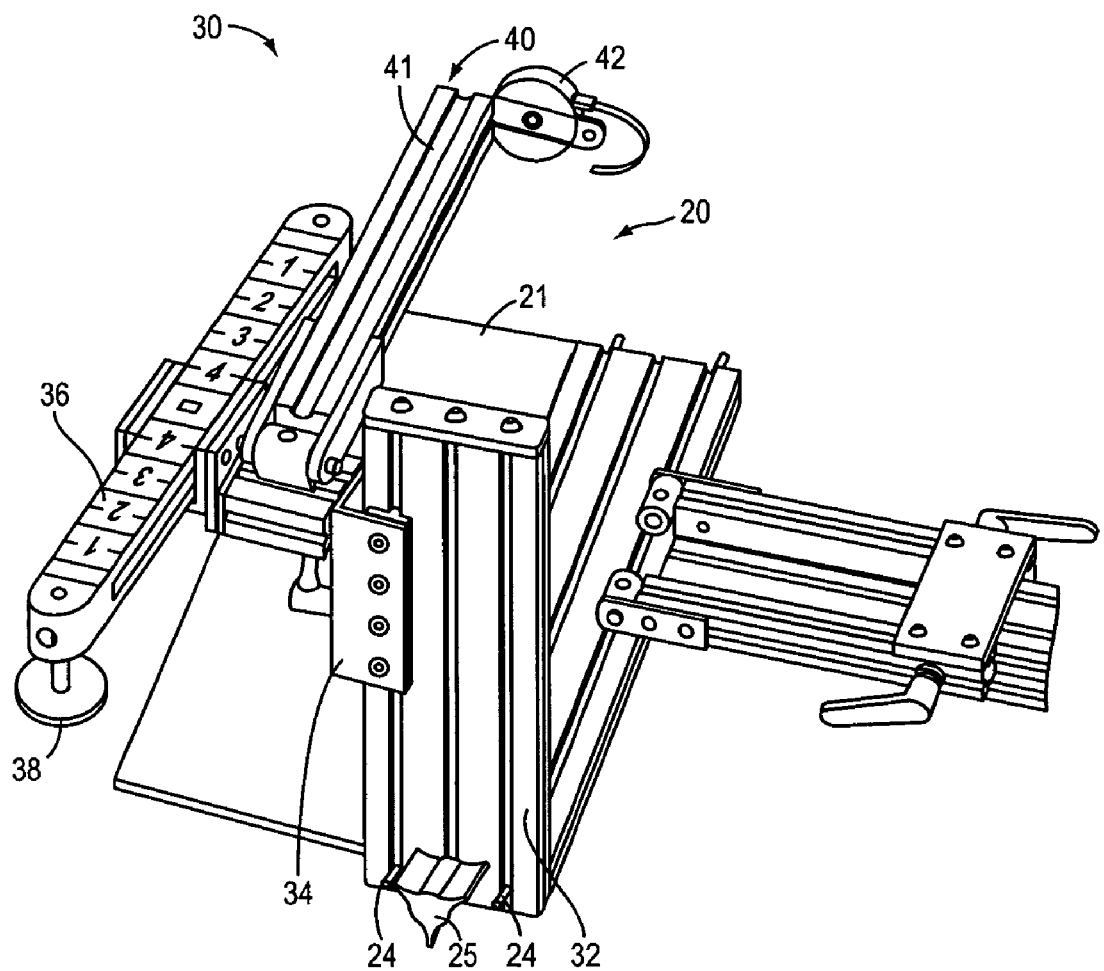
FIG. 6 is a drawing of the pelvic location assembly 30 according to the present invention.

Turning to FIG. 6, the pelvic location assembly 30 is attached to the planar portion 21 of the base 20, and is generally configured to provide the surgeon with a means for locating a point proximate the pelvic region of the patient. The pelvic location assembly 30 is attached to the base 20 on the side corresponding with the leg requiring treatment using locating pins 24 and fixing member 25. In the embodiment shown in FIG. 6, the pelvic location assembly 30 is attached to the right side of the base 20. But, as one of ordinary skill in the art will appreciate, the location assembly 30 may be positioned on the opposite side of the base 20 as desired.

The vertical support member 32 of the pelvic location assembly 30 is substantially elongate and has a vertical longitudinal axis. The lower end of the vertical support member 32 is rigidly attached to the stationary base 20, although it may be removed and reattached to the other side as necessary. Proximate the upper end of the vertical support member 32 is attached an adjustable frame member 34. This adjustable frame member 34 is configured to be rigidly attached relative to the vertical support member 32, but also adjustable along a portion of its length. Various members, including a skeletal reference location bar 36 and an alignment line assembly 40 are supported by the vertical support member 34. A skeletal reference locator 38 is located at each end of the skeletal reference location bar 36. As discussed elsewhere in this application, the skeletal reference locators 38 are configured to contact a certain portion of the body directly above a skeletal reference point, such as the anterior superior iliac spine.

Figure 7:
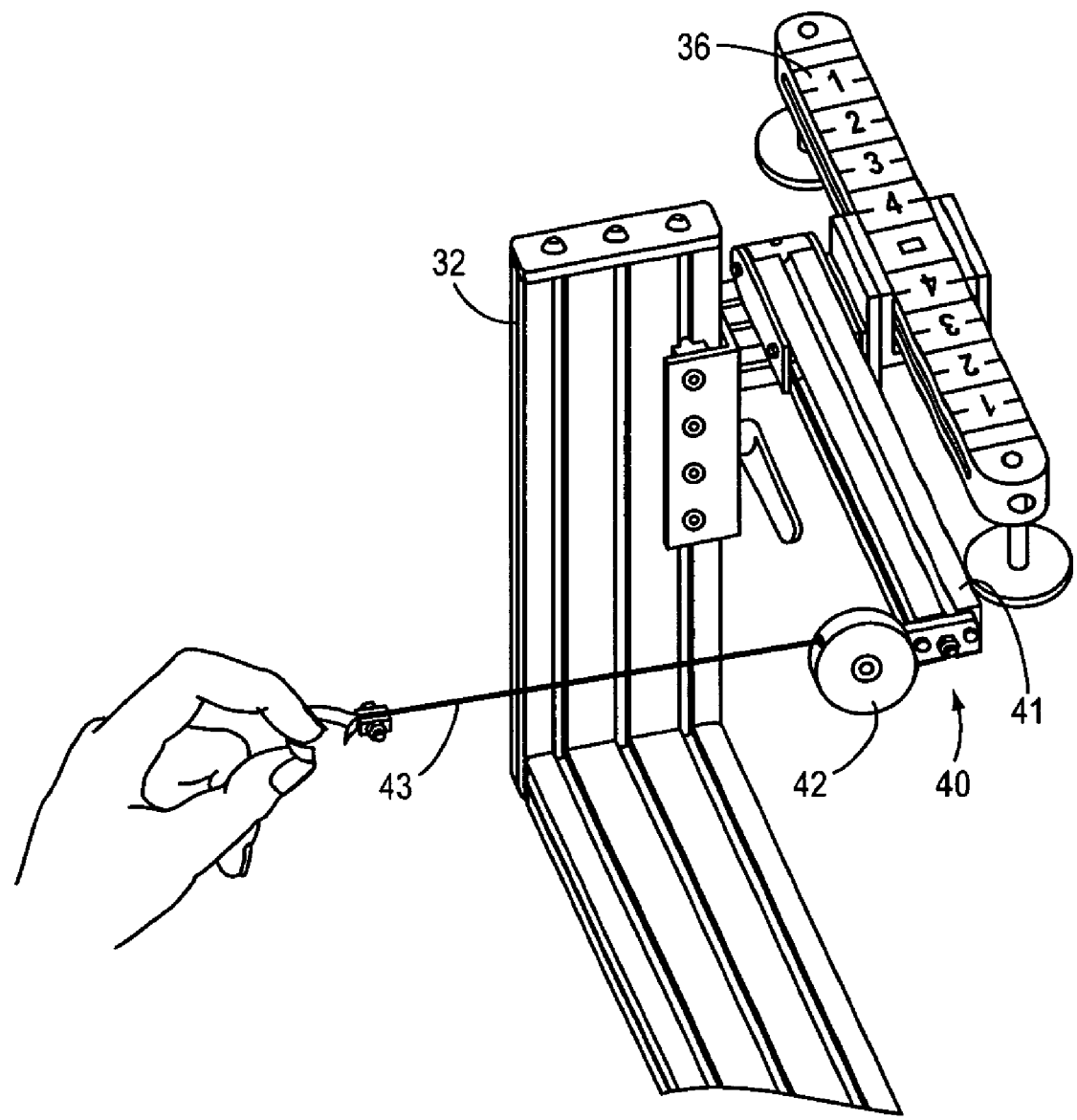
FIG. 7 is a drawing of a portion of the pelvic location assembly 30 showing the alignment line assembly 40 in accordance with one embodiment of the present invention.

As shown in FIG. 7, the alignment line assembly 40 includes an elongate member 41, an alignment reel 42, and an alignment line 43. The elongate member 41 has one end pivotably attached relative to the adjustable frame member 34, and has its opposing end attached to and supporting the alignment reel 42 and associated alignment line 43.

As discussed in detail later, the alignment line 43 when extended is used to provide a visual indication of a reference axis that is preferably substantially within the same vertical plane as the mechanical axis of the leg requiring treatment. An X-ray is taken of the patient and the distance between a skeletal reference point and the femoral head 1 is determined.

The location bar 36 is adjusted according to the determined distance using the scale positioned thereon. After the patient is positioned in the apparatus with their skeletal reference point adjacent the reference locator 38, the alignment reel 42 will be positioned proximate the center of the femoral head of the leg receiving treatment. In other words, the skeletal reference locator 38 is positioned a distance "d" from the alignment reel 42 using the scale located on the location bar 36.

Leg Manipulation Assembly 40

As shown in FIG. 5, the leg manipulation assembly 40 is configured to provide at least two functions. One function is to allow for suitable alignment of the leg, and the second function is to allow the leg to be bent into a position for surgical treatment while maintaining alignment. Referring generally to FIG. 4, for example, the leg manipulation assembly 40 generally includes an upper pivoting assembly 50, a lower pivoting member 80, and a carriage 90.

Upper Pivoting Assembly 50

Figure 8:
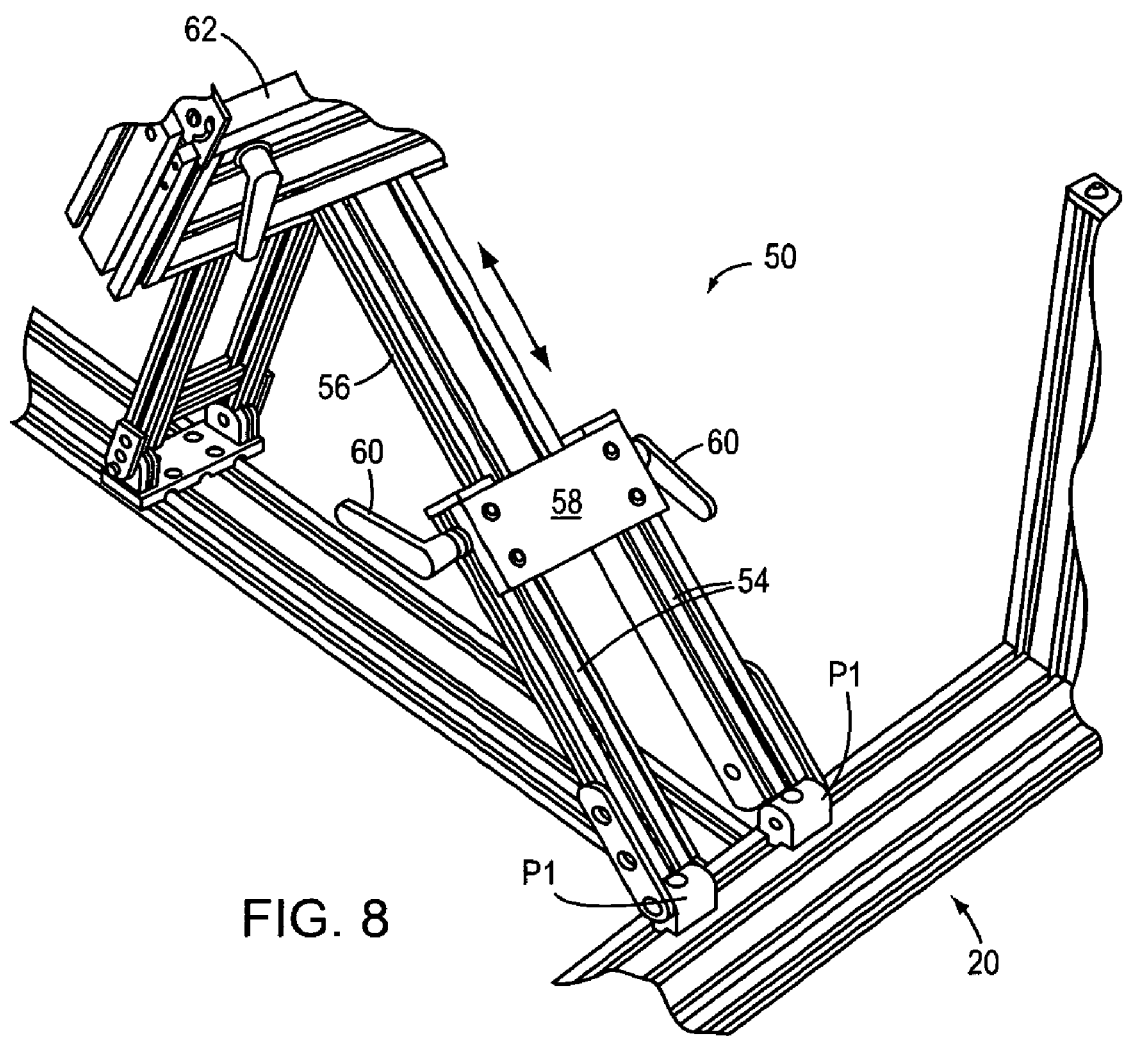
FIG. 8 is a drawing of a portion of the apparatus 10 focusing on the upper pivoting assembly 50 in accordance with an embodiment of the present invention.

Turning to FIG. 8, the upper pivoting assembly 50 is configured to be pivotably attached relative to the base 20 at pivot points P1. The upper pivoting assembly 50 is generally T-shaped. This member 50 includes a pair of lower parallel frame elements 54, an upper frame element 56, a connecting plate 58, a pair of length adjustment members 60 and a transverse member 62. The lower parallel frame elements 54 are each substantially elongate and have parallel longitudinal axes. The upper frame element 56 is likewise substantially elongate and has a longitudinal axis substantial parallel to those of the lower parallel frame elements 54. The connecting plate 58 attaches to the upper ends of the lower parallel frame elements 54. The length adjustment members 60 are configured to provide selective gripping between the lower frame elements 54 and the upper frame element 56, such that the overall length of the T-shaped upper pivoting assembly 50 may be varied as desired.

Figure 10:
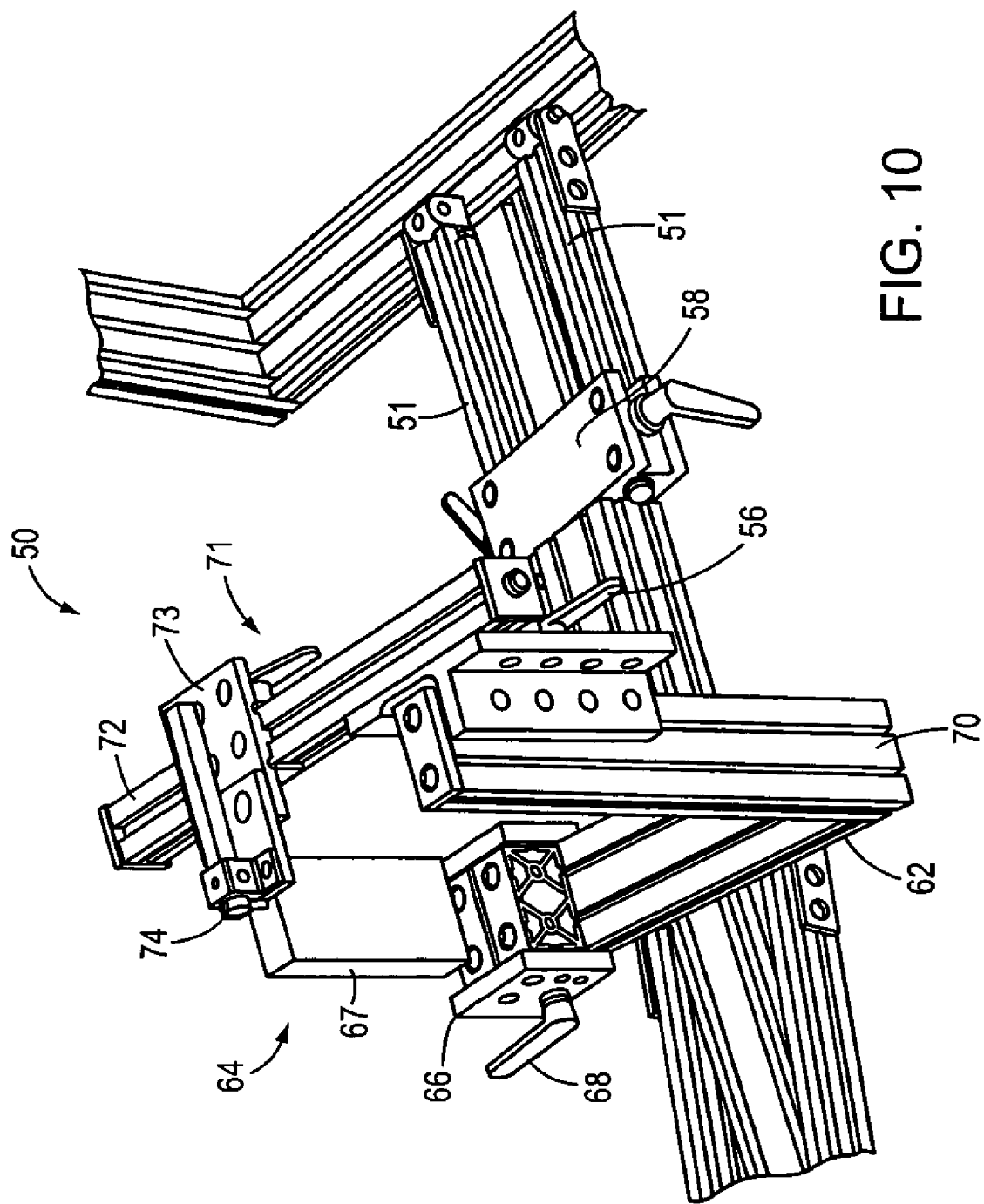
FIG. 10 is a drawing of a portion of the apparatus 10 focusing on the support column 70 and the cutting guide mounting assembly 71 in accordance with an embodiment of the present invention.
Figure 11:
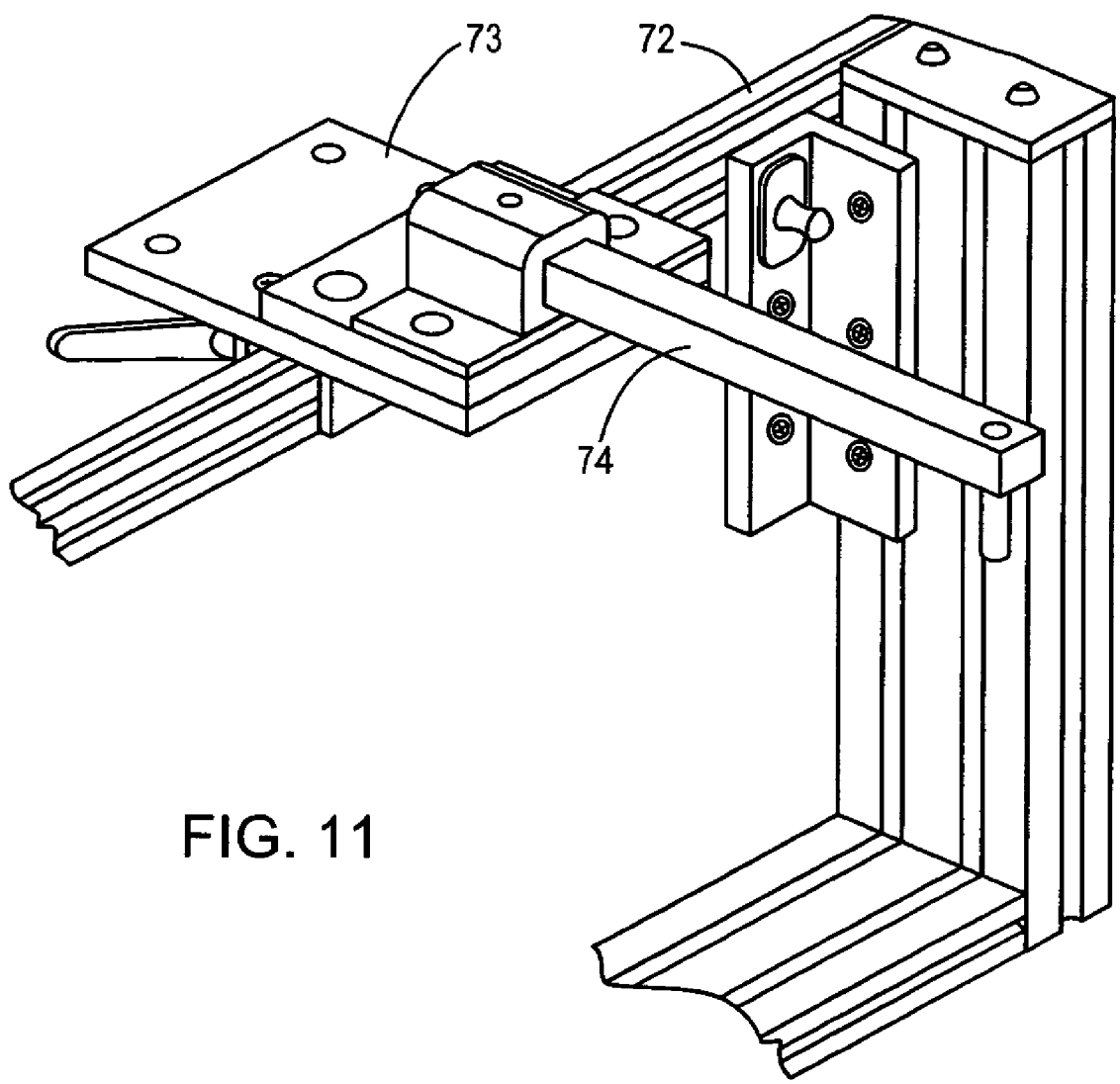
FIG. 11 is another view showing the cutting guide mounting assembly 71 similar to FIG. 10, but shows the cutting guide mounting assembly 71 in an extended state.

As shown in FIG. 10, the upper pivoting assembly 50 also includes an adjustable lateral force member 64 that includes a carriage 66, a padded flange 67 and a fixing member 68. As will be discussed elsewhere in this application, the carriage 66 allows for adjustment of the support member 64 relative to the transverse member 62 to facilitate manipulation of the leg. The fixing member 68 fixes the carriage 66 relative to the transverse member 62. Preferably, the longitudinal position of the lateral force member 64 is above the knee joint proximate the thigh portion of the patient's leg as is generally shown in FIG. 2A and 2B.

In a preferred embodiment, the lateral force member 64 is selectively locked in a position proximate the patient's leg and an inflatable bladder is positioned between the lateral force member 64 and the leg. The leg is urged away from the lateral force member 64 and into a desired alignment with the reference axis when the bladder is inflated, as will be discussed in greater detail later. Alternatively, a force may be applied to the lateral force member 64 in an axis parallel to the transverse member 62 and in the direction of the leg. This force will urge the leg is into a desired alignment with the reference axis after contact is made. At this point, the lateral force member may be selectively locked in place.

The upper pivoting assembly 50 also includes a support column 70 that extends from one end of the transverse member 62. Supported by the support column 70 is a cutting guide mounting assembly 71. This assembly 71 includes a cross member 72, an adjustment bracket 73, and a cutting guide mounting member 74. The cutting guide mounting member 74 will be discussed in more detail elsewhere in this application, as it provides a mounting structure for a cutting guide that aids the surgeon is cutting the femur and tibia in a desired axis and contour relative to the preferred mechanical axis.

Lower Pivoting Member 80

Figure 9:
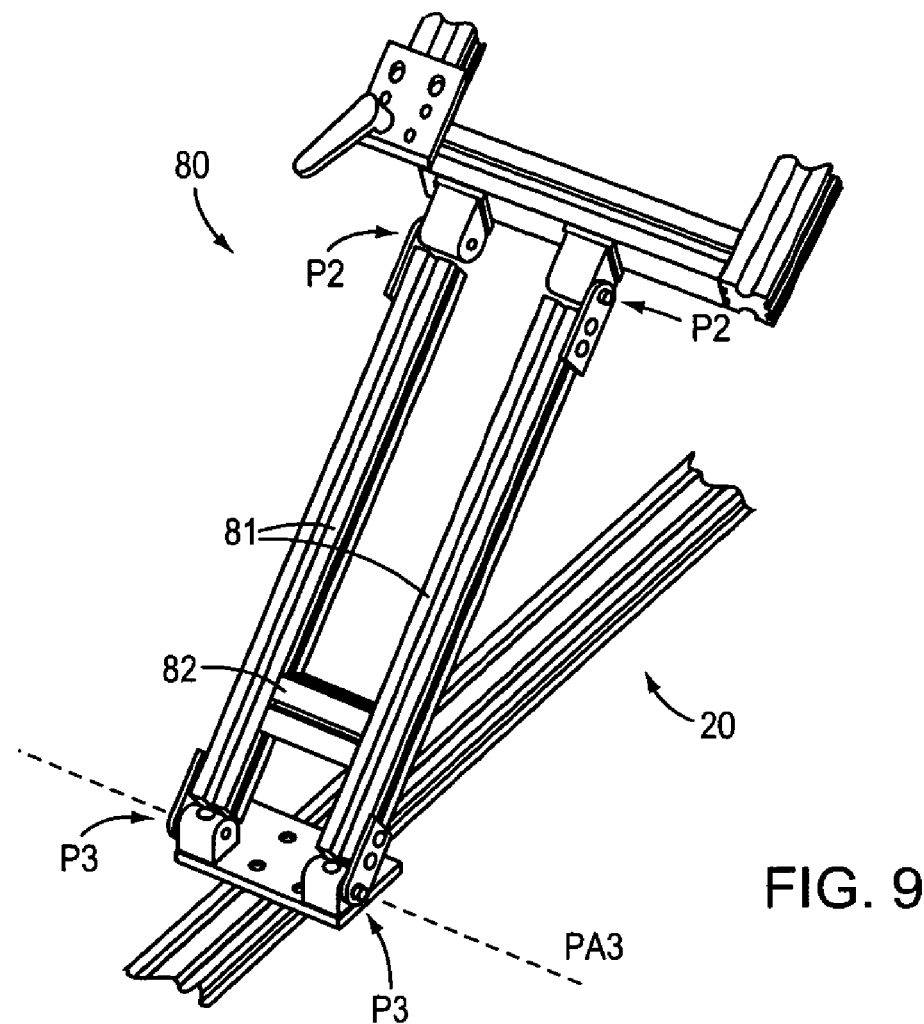
FIG. 9 is a drawing of a portion of the apparatus 10 focusing on the lower pivoting member 80 in accordance with an embodiment of the present invention.

Referring to FIG. 9, the lower pivoting member 80 has one end pivotably attached to the upper pivoting assembly 50 at pivot point P2 and has an opposite end attached relative to a carriage 90 at pivot point P3. The lower pivoting member 80 could be considered "H-shaped," in that it includes two parallel frame members 81 and a connecting cross member 82.

The lower pivoting members 80 are pivotably attached relative to the carriage 90 at pivot point P3. This carriage 90 is slidably mounted along the longitudinal axis of the spine member 22 of the stationary base 20. Alternatively, a ball bearing construction could be used as illustrated by the exemplary ball bearing 91 As may be understood, as the carriage 90 moves along the length of the spine member 22, a pivoting action is provided between the upper pivoting assembly 50 and the lower pivoting member 80, such as is illustrated by reference to the positions shown in FIGS. 4 and 5. This allows the leg positioned thereon to be bent to a greater or lesser degree as desired.

Foot Support Assembly 130

Returning to FIGS. 4 and 5, the foot support assembly 130 is adjustably attached relative to the spine member 22, such that it can be slid relative to, yet fixed to, the spine member 22 as desired. The foot support assembly 130 includes a carriage 132, a fixing member 134, a pivot pin 135, and a foot cradle assembly 136.

The carriage 132 provides a sliding action intermediate the foot support assembly 130 and the spine member 22. The fixing member 134 provides a fixing feature to fix the carriage 132 relative to the spine member 22.

Figure 12:
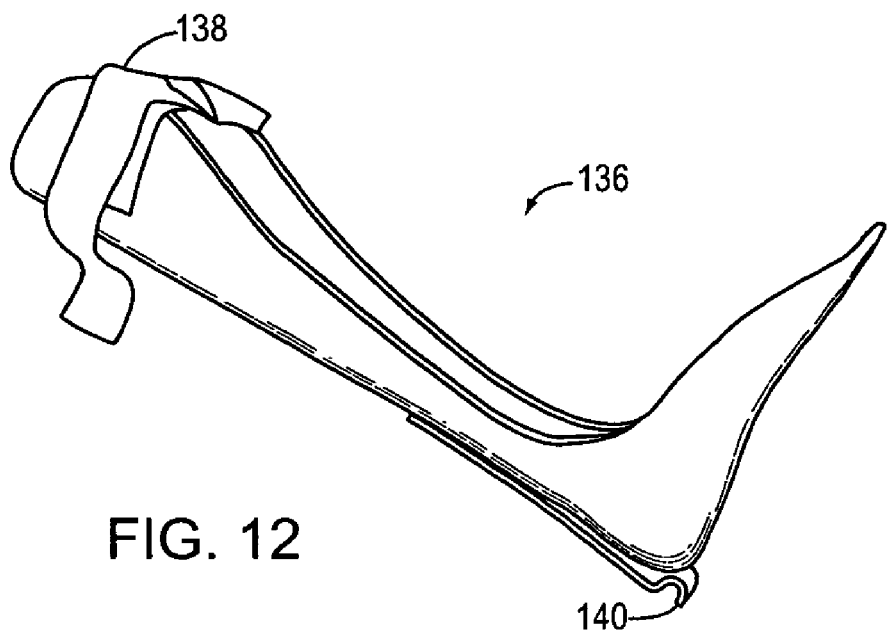
FIG. 12 is a drawing of the foot cradle assembly 136 without the carriage 90 in accordance with one embodiment of the present invention.

Turning to FIG. 12, the foot cradle assembly 136 is configured to accept a foot of a patient (not shown) and includes a retention strap 138 configured to retain the foot as and an attachment bracket 140. The attachment bracket 140 is configured to engage a pivot pin 135 on the carriage 132 such that a pivoting action is provided. By using a hook configuration, retention of the foot is provided while still allowing the foot to rotate about the axis of the pivot pin 135 when the leg is moved from its extended to its bent position. Furthermore, this attachment means also facilitates the application of a force on the leg of the patient along the axis of the spine away from the torso of the patient in order to stretch the knee joint ligaments and distract the knee joint.

Bladder Assembly 160

Working in conjunction with the rigid elements described above, a bladder assembly 160 provides a force to position a patient's leg into alignment as shown in FIGS. 3A and 3B.

Figure 14:
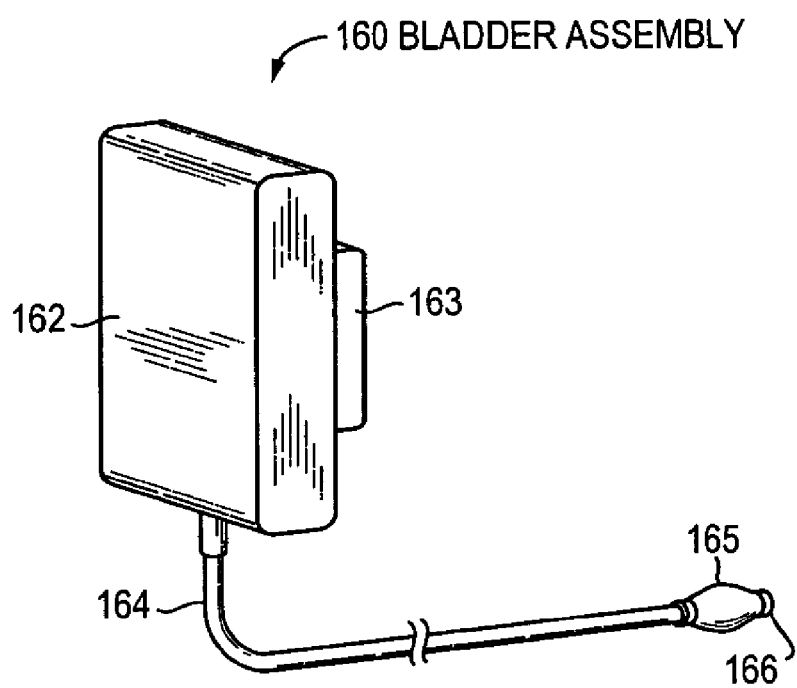
FIG. 14 is a drawing of an embodiment of the bladder assembly 160 in accordance with the present invention.

Turning to FIG. 14, the bladder assembly 160 generally includes a bladder 162, a retention sleeve 163, a tube 164, a bulb 165 and a valve 166. The bladder 162 is generally rectangular with the retention sleeve 163 attached thereto. The retention sleeve 163 is configured to slide over the padded flange 67 or attach to the support column 70. The tube 164 provides fluid communication between the bladder 162 and the bulb 165. Valve 166 controls the flow of air into and out of the bulb 165. As one of skill in the art will recognize, to inflate the bladder 162, the valve 166 is adjusted to allow air to flow in one direction into the bulb 165. As the bulb 165 is squeeze and released, air is forced into the bladder 162. To deflate the bladder 162, the valve 166 is adjusted to allow air to escape. The selective inflation and deflation of the bladder 162 allows the surgeon to position the patient's leg as desired.

Method of Operation

As previously described, the present invention is generally used to position a patient's leg into a desired alignment for surgery and/or treatment of the knee joint. The following paragraphs will describe the method of operation for an embodiment of the present invention.

Figure 15:
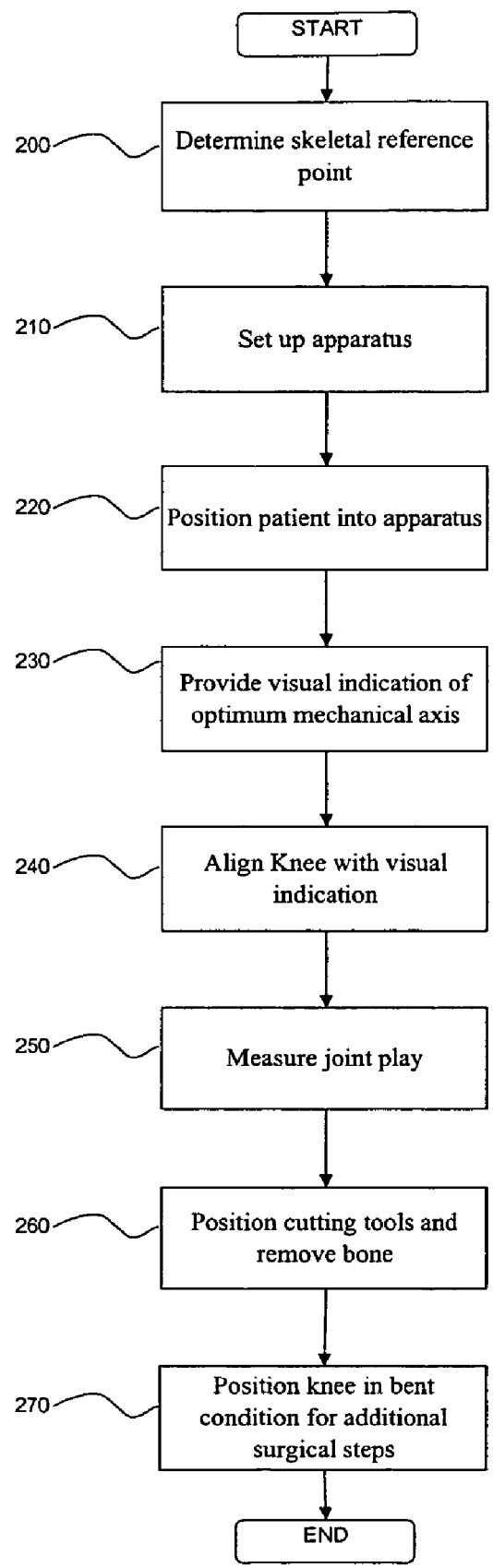
FIG. 15 is a flow diagram illustrating the steps of a method to align a leg in accordance with an embodiment of the present invention.

With reference to FIG. 15, the process begins at Step 200 where an X-ray of the patient is taken to determine the distance from a skeletal reference point to the femoral head of the leg requiring treatment. Preferably, the skeletal reference point is the anterior superior iliac spine.

Meanwhile, the apparatus 10 is placed on a substantially horizontal support surface such as the floor, a hospital bed or table at Step 210. Preferably, the weight of the patient will secure the device to the support surface. Alternatively, the device may be secured to the support surface with attachment brackets, straps or any other method of securing known in the art. The pelvic location assembly 30 is secured to the planar head 21 of the stationary base 20 on the side corresponding with the leg to be treated using securing member 25 and locating pins 24. In other words, if the right leg of the patent is being treated, the pelvic location assembly 30 is secured to the right side of the planar head 21. Then, the skeletal location bar 36 is adjusted according to the distance measurement from Step 200 using the scale located thereon.

At Step 220, the patient is positioned with his posterior on planar head 21 of the stationary base 20. The leg to be treated is positioned substantially parallel to the spine member 22 and between the adjustable lateral force member 64 and the support column 70. The patient is positioned such that the skeletal reference point on the patient's body is positioned proximate the skeletal locator 38. The upper pivoting assembly 50 is adjusted along its length such that the pivot axis PA2 is positioned proximate the knee of the patient.

The foot support assembly 130 is moved along the spine member 22 to allow the patient's foot 8 to be position therein. The patient's foot 8 is secured to the foot cradle assembly 136 using retention strap 138. The knee joint is then placed in tension by exerting a force on the foot support assembly 130 in a direction away from the patient's torso along the axis of the spine 22 and the foot cradle assembly 136 is secured to the spine member 22. This tension preferably extends the knee ligaments to their maximum length. At this point, the setup of the apparatus is complete and ready for determining the proper mechanical axis MA of the patient's leg 5.

At Step 230, the proper mechanical axis of a human leg is determined. To establish a reference axis within substantially the same vertical plane of the mechanical axis of the patient's leg, the elongate member 41 is pivoted towards the body and stops parallel with the skeletal reference location bar 36. Because the patient is positioned with the skeletal reference locator 38 proximate the skeletal reference point, the alignment reel 42 at the end of the elongate member 41 is located proximate the center of the femoral head of the leg receiving treatment when rotated into place. The alignment line 43 is then extended from the alignment reel 42 to the foot cradle assembly 136 to provide a visual indication of the reference axis. This reference is substantially within the same plane as the mechanical axis MA for the patient.

After identifying the proper mechanical axis MA for the patient's leg 5, the leg 5 is urged into a desired alignment with this visual axis at Step 240. To accomplish this alignment, a bladder assembly 160 is positioned on the lateral force member 64 and the support column 70. The bladder assemblies 160 are selectively inflated and contact a portion of the leg above the knee and proximate the thigh. The selective inflation urges the leg into alignment with reference axis and therefore into a desired alignment with the mechanical axis. Preferably, the patient's leg is positioned in a desired alignment with the reference axis when the reference axis is slightly to the medial side of the knee portion of the leg. At this step in the process, the leg is held in the proper mechanical axis as indicated by the reference axis established in Step 230. After the leg is secured in the proper mechanical axis by the external framework, the alignment line 43 may be retracted into the alignment reel 42 and the surgical procedure and/or treatment may begin.

As discussed earlier in this application, a typical surgical procedure on the knee joint is the application of a prosthesis for all or a portion of the bearing surfaces. To accommodate a prosthesis, all or a portion of the bearing surfaces of the femur and tibia must be removed as shown in FIG. 1.

Unicompartmental knee or partial replacement requires that a portion of the medial tibia and the medial femoral condyle be removed to accommodate the new bearing surface. The cuts in the end of the tibia and the end of the femur are preferably perpendicular to the mechanical axis and thus necessarily parallel to each other when the knee is in full extension. Further cuts in the end of the femur may be necessary to accommodate the typically curved femoral bearing surface or femoral prosthesis which is typically made from metal but could be fashioned from other materials including human tissue. With a unicompartmental knee replacement there is always a saggital or side cut which extends from the usual planar cut at the end of the bone into the joint such that only half of the distal femur and half of the proximal tibia is cut.

The Total Knee Replacement requires that the entire proximal tibia and the entire distal femur be cut in order to accommodate for the new tibial and femoral bearing surface or prosthesis. Again there may be necessary cuts in the femur to bevel the end of the femur to accommodate for a bearing surface or prosthesis that is curved in nature. Certainly, the cutting guide mounting assembly 71 could accommodate other cutting guides for removal of small portions of the joint for smaller or partial surface bearing replacements to occur.

Before making any cuts to the bone, the surgeon will determine the amount of clearance in the joint needed for proper operation of the prosthesis. At Step 250, the clearance between the femur and the tibia of an undamaged portion of the knee is measured using the measurement tool 150. If the surfaces of the knee requiring treatment are damaged for example for a total knee replacement, the surgeon may measure the spacing in the other knee to use as a reference.

To check the "play" in the knee joint, the patient is positioned in the apparatus 10 with the leg receiving treatment aligned with the proper mechanical axis and distracted. The measurement tool 150 is positioned between the bearing surfaces of the femur and tibia to determine the distance between the bearing surfaces. From this measurement, the surgeon can calculate the amount of bone that needs to be removed from the ends of the femur and tibia for proper positioning of the prosthesis. This calculation includes the space required by the prosthesis plus the distance measured between the bearing surfaces. For example if one millimeter of joint clearance is desired and the overall thickness of the prosthesis is twenty millimeters, then ten millimeters of tibia and eleven millimeters of femur will be is removed to achieve the desired 1 mm clearance.

To assist the surgeon in determining the proper amount of bone to remove, a spacer having the thickness of the desired joint play may be inserted between the bearing surfaces of the prosthesis joint. Using this technique, the surgeon simply measures the prosthesis with the spacer in place to obtain the space necessary to receive the prosthesis and to create the optimum joint play. The spacer itself may be made of a conventional dissolvable material and attached to one of the bearing surfaces of the prosthesis joint. In this embodiment, the desired joint play will be present when the spacer dissolves shortly after the surgery. Additionally, the dissolvable space may include an antibiotic or other factors that release as the spacer is dissolved to promote the healing of the knee. Alternatively, the spacer may be made of a non-dissolvable material such as metal or plastic and remove by the surgeon after insertion of the prosthesis.

In preparation for removing bone, the cutting guide mounting member 74 and the adjustment bracket 73 are adjusted to position cutting guides proximate the proximal end of the tibia at Step 260. These cutting guides are preferably held perpendicular to the mechanical axis MA. A cutting saw or routing tool is then used to remove the desired amount of bone from the tibia. This procedure is repeated for the distal end of the femur.

After the cuts are made, the cut surfaces must be shaped to accept the prosthesis at Step 270. Typically this requires beveling the cut surfaces of the bone. To accomplish this task, the leg is positioning by the apparatus 10 in the bent condition. The fixing member 134 of the foot support assembly 130 is release and the leg manipulation assembly 40 is pivoted upwardly by directing a force at pivot point PP2 in an upward direction. This causes the foot support assembly 130 and the carriage 90 to slide along the spine member 22 toward the patient's torso. After the desired degree of bend is achieved, the fixing member 134 secures the foot cradle assembly 130 to the spine member 22 while still allowing the foot cradle assembly 130 to pivot relative the pivot pin 135. As may be understood, a bladder may be positioned under the thigh when the leg is in the bent position in order to provide distraction to the knee to allow for finishing cuts on the bone and/or installation of various prosthetic devices.

A conventional beveling tool is then used to shape the cut ends of the bone to accept the prosthesis. These tools typically use the cut surface as a guide for the beveling operation. After beveling and with the knee in a bent position, the prosthesis is positioned on the cut surfaces of the tibia and femur. The leg is then returned to a straight condition and the ligaments of the knee compress the prosthesis.

Variations

As may be understood, the present invention contemplates variations in configuration and use. For example, instead of using bladders to position the knee, a force may be applied directly to the adjustable lateral force member 64 and therefore onto the leg until the leg is in alignment with the proper mechanical axis MA. In this embodiment, lateral force members 64 are slideably attached to transverse member 62 such that the patient's leg would be positioned between the two support members 64. Referring briefly to FIG. 3A, the two padded flanges 67 are placed against the medial and lateral aspect of the distal femur. Using these two padded flanges the knee is pushed or pulled such that the leg is urged into alignment with its proper mechanical axis MA. Each flange is then locked into place on the transverse member 62 using fixing members 68. This assures that the knee will remain in the patient's optimal mechanical position. It also allows the cross member 72 of the apparatus 10 to remain in a plane perpendicular to the patient's knee allowing surgical cuts to be made accurately with respect to the mechanical axis MA. Additionally, during the surgical procedure, conventional skin and/or soft tissue retractors can be attached to these medial and lateral pads to allow easy and assistant-free access to the inside of the knee.

In a further variation, a routing tool may be to the external frame instead of cutting guides as described elsewhere in this application. In this embodiment, the knee is positioned in the apparatus 10 such that the leg is fully extended and aligned with the mechanical axis as described above. Once the knee is properly aligned in the device, an operating arm supporting the routing tool is attached to the support column 70 such that the arm is fixed in a plane perpendicular to the mechanical axis MA and lies anterior to the knee. This operating arm can be moved superiorly and inferiorly along the MA. It can also move anterior and posterior relative to the knee. During these movements, the arm preferably remains perpendicular to the MA of the leg.

Generally, a "flat walled" drill or router bit is used which has a substantially round and constant cutting circumference. By rotating the router bit about its longitudinal axis and moving it along an axis perpendicular to its rotational axis, a flat wall may be formed on the bone if the router is drawn past an uneven surface.

An end and side cutting bit attached to a high speed drill or router can be attached to the operating arm such that it can slide medial and lateral along the line of the arm. When the drill is lowered to a bone in the knee and the drill is moved along the operating arm medial and lateral, the end and side cutting bit will create a flat surface cut in the bone along the plane that is perpendicular to the mechanical axis. As the bit is lowered more and more posteriorly the bone can be cut in two leaving the end of the bone perfectly flat with a surface that is perpendicular to the MA. Thus, when the patient is standing the flat cut at the end of the tibia and the end of the femur will be generally parallel to the floor.

As an alternative, the routing tool could be made to rotate about a fixed position on the operating arm thereby creating a cutting arc which is preferably perpendicular to the MA.

Typically, the tibia is cut first followed by the femur. The exact distance between the distal femoral cut and the proximal tibia cut should equal the thickness of the knee prosthesis to be inserted plus the amount of normal play desired in the joint.

Once the end of the femur is cut in the above fashion it must be shaped to fit the prosthesis. In the apparatus 10, the femur is lifted up and the knee bent and rigidly fixed. Once in this position, the foot support assembly 130 is secured to the spine member 22. A bladder is inflated underneath the thigh such that the thigh is moved away from the upper pivoting assembly causing the femur to be lifted away from the proximal tibia. This creates a distraction force that lifts the end of the femur off of the tibia.

Once the knee is bent and distracted, the cut ends of the femur and tibia can be shaped or a secondary cut made so the cut surfaces of the bone conform to the mating surfaces of the prosthesis. For example, an end and side cutting bit can be positioned in a routing tool to create the necessary flat surfaces relative to the original cut surface of the femur for any and all varieties of knee prosthesis.

In some situations, a patient may not be able to extend the knee completely, resulting in a condition known as "flexion contracture." Assuming that the knee has a 10 degree bend in it, the surgeon can bisect the remaining bend and pivot the router about the operation arm 5 degrees in order to provide a cut on the tibia. Typically the leg will then fall into a straight position and the surgeon can continue as described elsewhere. The initial cut to the tibia can, if needed, be revisited and re-cut if needed.

Figure 16:
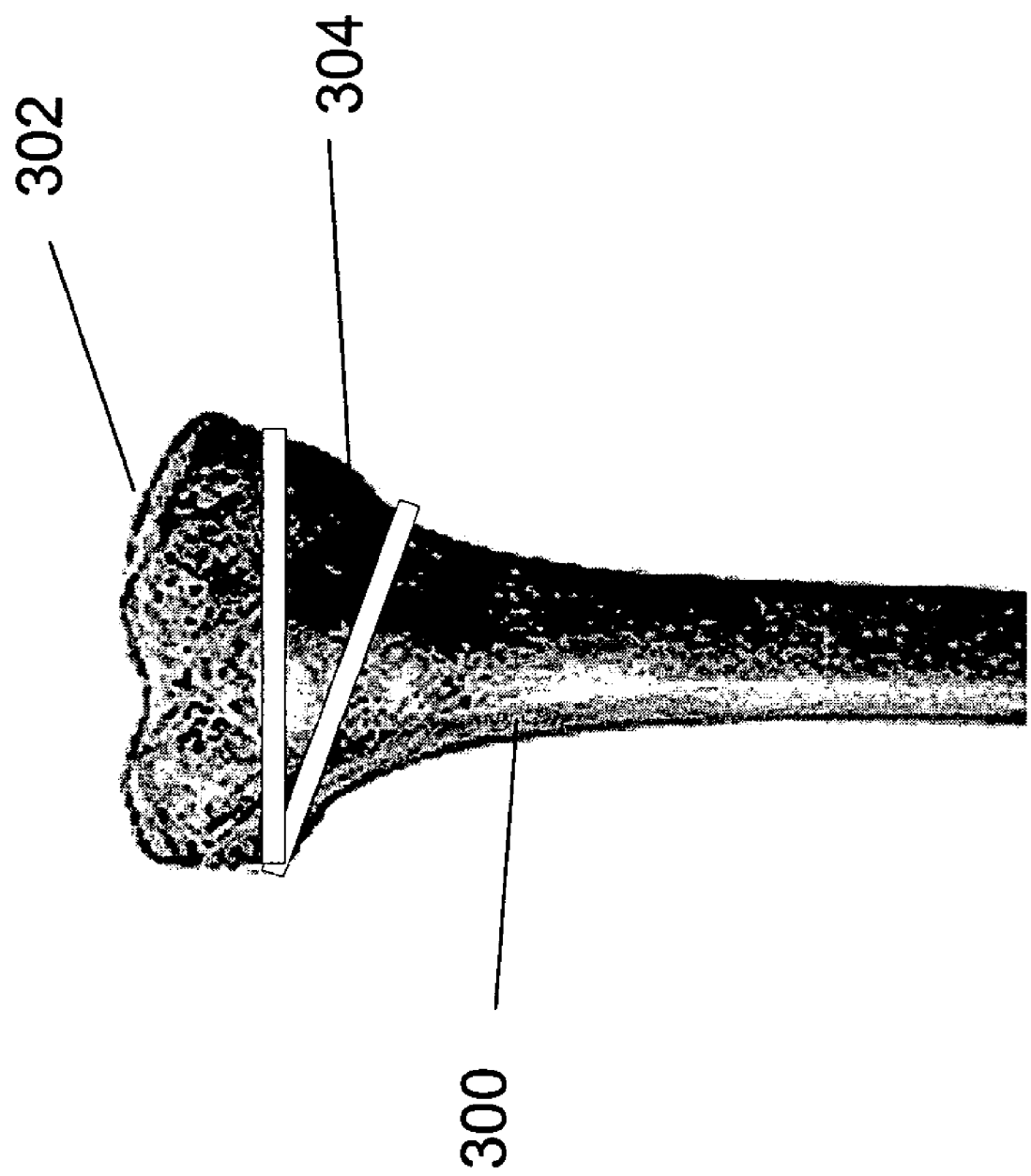
FIG. 16 is a drawing of a portion of a tibia 300 illustrating two cut lines for an osteotomy procedure.
Figure 17B:
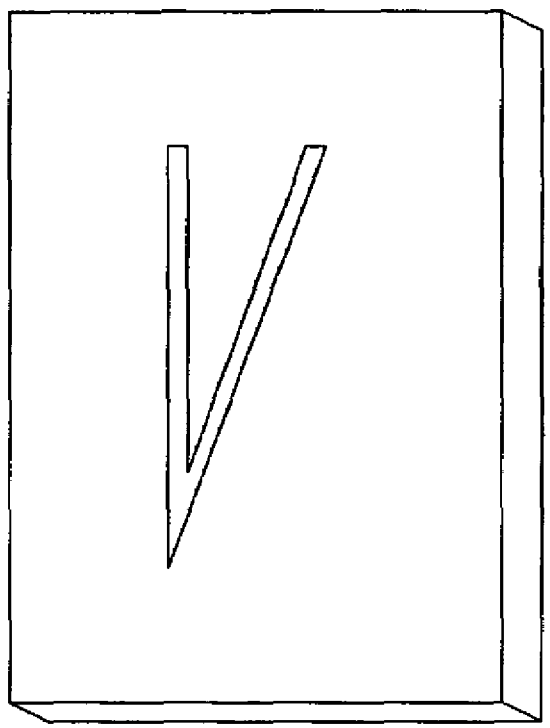
FIGS. 17A and 17B illustrate cutting guides having slots therein in accordance with an embodiment of the present invention.
Figure 17A:
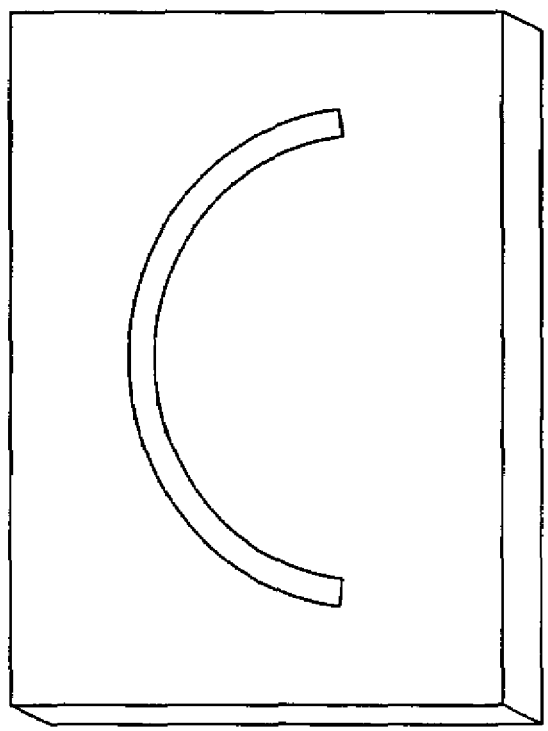

In addition to total or unicompartmental knee arthoplasty, the present invention may be used in an osteotomy procedure which is performed to correct a varus or valgus deficiency. With reference to FIG. 16, a conventional osteotomy procedure includes removing a wedge portion 304 from the tibia 300 at a location space apart from the bearing portion 302 of the tibia 300. After the wedge portion is removed, the bearing portion 302 is reattached to the remaining tibia 300 using a metal plate and screws. To facilitate the proper wedge shape, a cutting guide providing a wedged shaped template as shown in FIG. 17A may be positioned using an embodiment of the present invention.

In addition to the wedge shaped cut, domed or arcuate cut osteotomy procedures have been performed, but with limited success due to the difficulty in achieving an arcuate cut manually. An embodiment of the present invention provides a cutting guide with an arcuate slot as shown in FIG. 17B and an external frame to position the cutting guide to improve the accuracy of the domed or arcuate cut.

Figure 18:
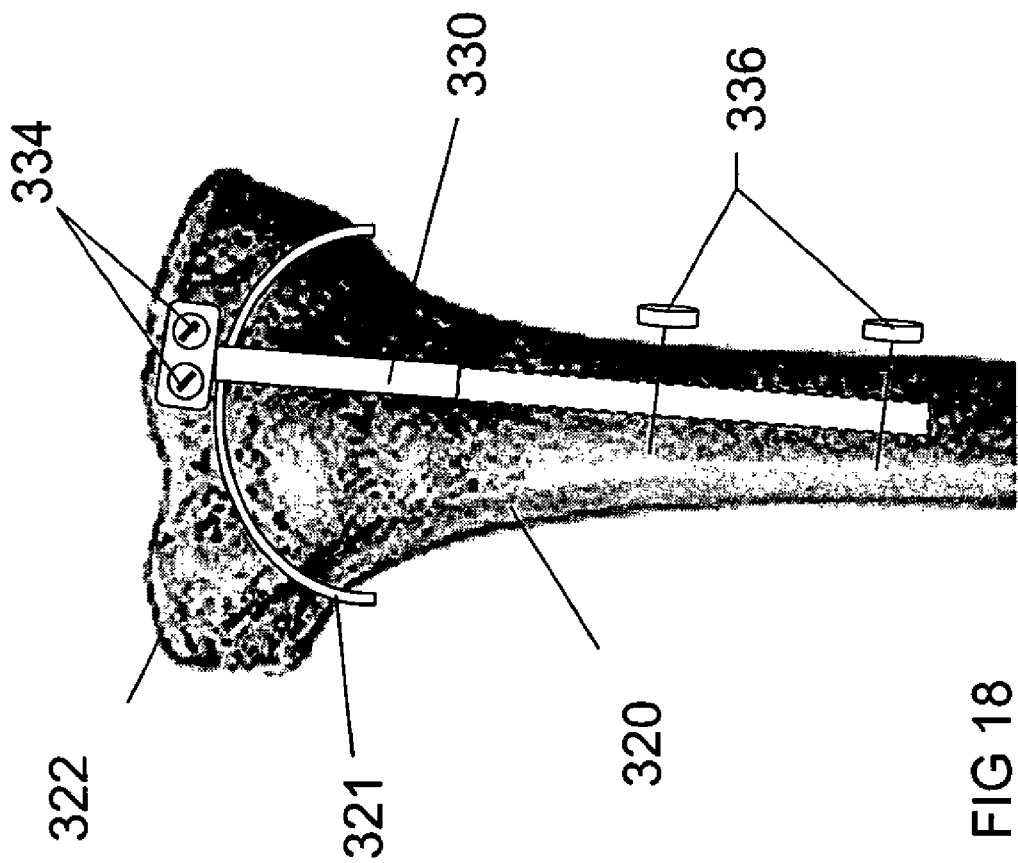
FIG. 18 is a drawing of a tibia and a retention rod 330 in accordance with an embodiment of the present invention.

In the domed cut osteotomy, an arcuate cut 321 is made in tibia 320 as best shown in FIG. 18. The bearing surface portion 322 of the tibia 321 is then rotated into the desired location. To secure the two portions of the tibia in a desire location, a retention rod 330 is used.

Figure 19:
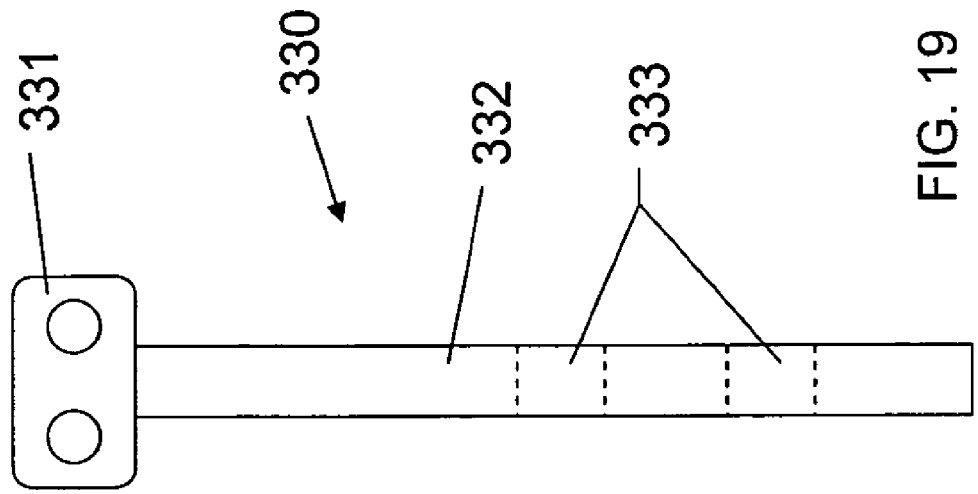
FIG. 19 is a drawing of a retention rod in accordance with an embodiment of the present invention.

Referring to FIG. 19, the retention rod is a generally "T" shaped member having a transverse head portion 331 and an elongate portion 332. The transverse portion 331 is configured to accept convention fasteners. The elongate portion 332 includes a plurality of slots 333 configured to accept convention fasteners while still allowing movement in a direction parallel with the elongate axis of the retention rod 330. As one of ordinary skill in the art will appreciate, any number of fasteners may be used to secure the rod 330 to the bone. Furthermore, the rod shape may be formed to follow more closely the contour of the bone as desired.

After the two portions of the tibia are positioned in a desired location, the elongate portion of the retention rod 330 is partially inserted into the tibia as generally shown by dashed lines in FIG. 18. Fasteners 336 are driven into the tibia 320 and through the slots 333 to secure the retention rod 330 to the tibia 320 while still allowing movement of the rod in its longitudinal axis. The bearing surface portion 322 of the tibia 320 is secured to the head portion 331 of the retention rod 330 using convention fasteners.

The domed cut osteotomy procedure is beneficial because there is minimal loss in tibia length and there is greater surface contact area for healing than with the wedge cut procedure. Furthermore, the retention rod attachment discourages relative movement of the tibia 320 and the bearing surface portion 322 both rotationally and laterally in a plane perpendicular to the longitudinal axis of the rod. However, this attachment method allows some movement in the axis parallel to the retention rod 332 due to the use of slots 333 to attach the rod to the tibia 320.

Adjustments

The present invention has several adjustments to accommodate a variety of patient sizes and shapes. During the initial setup, the foot cradle assembly 130 may be adjusted along the length of the spine member 22 to accommodate varying leg lengths. Similarly, the length of the upper pivoting assembly 50 may be adjusted to position the pivot point PP2 under the knee. This allows the invention to accommodate patients with different femur lengths.

The pelvic location assembly 30 also provides adjustments for varying waist measurements. As discussed earlier in this application, the adjustable frame member 34 allows for vertical adjustment of the skeletal reference location bar 36 along the length of the vertical support member 32 to accommodate girth variations between patients.

The present invention also includes provisions for adjusting the location of cutting guides. These provisions include a vertical adjustment of the cutting tool mounting assembly 71 that allows the surgeon to position the guides at a desired distance above the knee joint. The cutting guide mount assembly 74 itself also provides adjustments laterally (i.e. perpendicular to the elongate axis of the leg) and longitudinally (i.e. parallel elongate axis of the leg) allowing the surgeon to position the guides as desired.

Additionally, the apparatus may be configured for use on either leg. This is accomplished by moving the pelvic location assembly 30 from one side of the planar head 21 to the other. In other words, if the right leg of the patent is being treated, the pelvic location assembly 30 is secured to the right side of the planar head 21.

To position the pelvic locating assembly 30, the present invention provides two locating pins 24 on each side of the planar head 21 as best shown in FIG. 6. The pelvic location assembly is configured to accept the locating pins and provides a securing member 25 to retain the pelvis location assembly 30 to the planar head 21 of the stationary base 20.

That which is claimed:

1. An apparatus for aligning a leg of a patient with a mechanical axis to facilitate medical treatment thereon, said leg including a femoral head, a thigh portion and a foot portion which itself includes an ankle portion, said mechanical axis having a portion extending from the center of said femoral head to the center of said ankle, said apparatus comprising:
   a base member including a spine portion and a head portion, said spine portion being substantially elongate and having a longitudinal axis, said head portion attached proximate one longitudinal end of said spine portion;
   a pelvic location assembly attached relative to said base member proximate said head portion, said pelvic location assembly including a femoral head location member configured to establish a first reference point positioned at a known location relative to the center of said femoral head;
   a carriage moveably attached relative to said spine portion and configured to be moved along a carriage path having a portion being substantially parallel to said longitudinal axis of said spine portion said carriage further configured to be selectively secured relative to said spine portion so as to discourage said relative movement between said carriage and said spine portion;
   a boot assembly pivotably attached relative to said carriage and configured to accept said foot portion of said leg and to establish a second reference point at a known location relative to the center of said ankle portion;
   a mechanical axis indicator providing a visual indication of a portion of a reference axis passing from said first reference point to said second reference point, such that said reference axis is within substantially the same plane as said mechanical axis; and
   a leg manipulation assembly attached relative to said spine portion between said pelvic location assembly and said boot assembly, said leg manipulating assembly having a first lateral force assembly and a second lateral force assembly, said force assemblies being proximate said thigh portion and spaced apart to accept said leg therebetween, said first lateral force assembly being adjustable and selectably securable along an axis substantially perpendicular to said longitudinal axis of said spine portion and configured to discourage said leg from moving away from a desired alignment with said mechanical axis indicator.

2. The apparatus of claim 1, wherein said leg also includes a knee, and wherein said first lateral force assembly includes a first post member and a first inflatable bladder, said first inflatable bladder being positioned between said first post member and said leg such that inflation of said first bladder tends to cause said first bladder to bias against said leg proximate said knee such that said knee tends to move away from said first post member;

wherein said second lateral force assembly includes a second post member and a second inflatable bladder, said second inflatable bladder being positioned between said second post member and said leg such that inflation of said second bladder tends to cause said second bladder to bias against said leg proximate said knee such that said knee tends to move away from said second post; and wherein said first and second bladders are configured such that selectively inflating said first and said second bladders tends to provide a bias between said leg proximate said thigh portion and at least one of said first and said second bladders, thus urging said knee into a desired alignment with said mechanical axis indicator.

3. The apparatus of claim 2, wherein selectively inflating said first and said second bladders discourages movement of said leg relative to said first and said second post members.

4. The apparatus of claim 1, wherein said first lateral force assembly includes a first post member moveably attached relative to said base member such that said first lateral force is adjustable and selectively securable in an axis substantially perpendicular to the longitudinal axis of said spine portion;

wherein said second lateral force assembly includes a second post member moveably attached relative to said base member such that said second lateral force member is adjustable and selectively securable in an axis substantially perpendicular to the longitudinal axis of said spine portion and spaced apart from said first post member to accept said leg therebetween; and wherein further said first and second part members are configured to contact said leg and are configured to urge a knee of said leg into alignment with said mechanical axis indicator.

5. The apparatus of claim 4, further comprising a cutting guide mounting assembly attached relative to said first post member and configured to position a cutting guide proximate a knee portion of said leg.

6. The apparatus of claim 5, wherein said cutting guide mounting assembly is adjustable in at least two orthogonal axes.

7. The apparatus of claim 5, wherein said cutting guide mounting assembly is configured to facilitate bone removal in an axis perpendicular to said mechanical axis.

8. The apparatus of claim 5, wherein said cutting guide includes an arcuate slot configured to provide a path for a bone cutting tool to follow.

9. The apparatus of claim 5, wherein said cutting guide includes a wedge shaped slot configured to provide a path for a bone cutting tool to follow.

10. The apparatus of claim 1 further comprising an operating arm configured to secure a cutting tool and to provide movement of said cutting tool in at least two axes.

11. The apparatus of claim 10, wherein said operating arm is configured to pivotably secure said cutting tool, wherein further said cutting tool pivots about an axis substantially parallel to said longitudinal axis of said spine portion.

12. The apparatus of claim 1, for aligning said leg of said patient, said leg also including a knee portion, wherein said leg manipulation assembly includes:

an upper pivoting assembly having a first end and a second end and including a thigh support portion, said upper pivoting assembly including said first and said second lateral force assemblies spaced apart to accept said leg therebetween, said first end being pivotably attached relative to said spine portion proximate said head portion and said first and second lateral force assemblies being positioned proximate said second end such that they can pivot together relative to said spine portion while still retaining said leg therebetween;

a carriage slidably mounted along the longitudinal axis of said spine portion; and a lower pivoting member having a first end and a second end, said first end of said lower pivoting member being pivotably attached to said second end of said upper pivoting assembly proximate said patient's knee portion, said second end of said lower pivoting member being pivotably attached to said carriage, said upper pivoting assembly, lower pivoting member, and said carriage configured to be moved from a first, "straight-leg" configuration, in which said first and second lateral force assemblies retain said leg therebetween while said leg of said patient is substantially straight, to a second, "bent-leg", configuration, in which said first and second lateral force assemblies retain said leg therebetween while said leg of said patient is bent and while said thigh support portion provides support proximate said thigh portion of said leg, said upper pivoting assembly pivoting about its said first end when moving from said first to said second configuration.

13. The apparatus of claim 12, wherein the length of said upper pivoting assembly between its said first and second ends can be adjusted in length to allow adjustability to accommodate the length of a patent's leg such that the position of said first and second lateral force assemblies can be adjusted together relative to the leg of said patient.

14. The apparatus of claim 12, wherein said thigh support portion is configured to allow free movement of a calf portion of said leg when said leg is in said bent condition.

15. The apparatus of claim 12 further comprising an inflatable bladder positioned intermediate said thigh portion and said upper pivoting assembly to encourage distraction of said knee joint when knee is in a bent condition and said bladder is selectively inflated.

16. The apparatus of claim 1, for aligning said leg of said patient, said leg also including a knee portion, wherein said leg manipulation assembly is configured to be moved from a first, "straight-leg" configuration, to a second, "bent-leg", configuration, while still tending to retain the leg in desired alignment with said mechanical axis.

* * * * *

UNITED STATES PATENT AND TRADEMARK OFFICE
CERTIFICATE OF CORRECTION

PATENT NO. : 7,665,167 B2 Page 1 of 1
APPLICATION NO. : 11/077964
DATED : February 23, 2010
INVENTOR(S) : Branch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1382 days.

Signed and Sealed this

Seventh Day of December, 2010

David J. Kappos
*Director of the United States Patent and Trademark Office*